(12) United States Patent
Dey et al.

(10) Patent No.: US 12,252,484 B2
(45) Date of Patent: Mar. 18, 2025

(54) PYRAZOLOPYRIDINE COMPOUNDS FOR THE TREATMENT OF AUTOIMMUNE DISEASE

(71) Applicant: Hoffmann-La Roche Inc., Little Falls, NJ (US)

(72) Inventors: Fabian Dey, Basel (CH); Taishan Hu, Shanghai (CN); Haixia Liu, Shanghai (CN); Hong Shen, Shanghai (CN); Zhiwei Zhang, Shanghai (CN); Wei Zhu, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 705 days.

(21) Appl. No.: 17/274,035

(22) PCT Filed: Sep. 6, 2018

(86) PCT No.: PCT/EP2018/073929
§ 371 (c)(1),
(2) Date: Mar. 5, 2021

(87) PCT Pub. No.: WO2020/048596
PCT Pub. Date: Mar. 12, 2020

(65) Prior Publication Data
US 2021/0355122 A1    Nov. 18, 2021

(51) Int. Cl.
*C07D 471/04* (2006.01)
*C07D 471/08* (2006.01)
*C07D 471/18* (2006.01)
*C07D 498/18* (2006.01)
*C07D 519/00* (2006.01)

(52) U.S. Cl.
CPC ......... *C07D 471/04* (2013.01); *C07D 471/08* (2013.01); *C07D 471/18* (2013.01); *C07D 498/18* (2013.01); *C07D 519/00* (2013.01)

(58) Field of Classification Search
CPC .. C07D 471/04; C07D 471/08; C07D 471/18; C07D 498/18; C07D 519/00; A61P 37/00
See application file for complete search history.

(56) References Cited

U.S. PATENT DOCUMENTS

| | | |
|---|---|---|
| 9,902,702 B2 | 2/2018 | Ladziata et al. |
| 10,544,143 B2 | 1/2020 | Dyckman et al. |
| 10,640,500 B2 | 5/2020 | Boivin et al. |
| 2013/0324547 A1 | 12/2013 | Boivin et al. |
| 2015/0105370 A1 | 4/2015 | Carlson et al. |
| 2017/0174653 A1 | 6/2017 | Sherer et al. |
| 2018/0037570 A1 | 2/2018 | Sherer et al. |
| 2019/0185469 A1 | 6/2019 | Dyckman et al. |
| 2021/0269451 A1 | 2/2021 | Liu et al. |
| 2021/0340134 A1 | 4/2021 | Qui et al. |
| 2021/0340136 A1 | 4/2021 | Zhu et al. |
| 2021/0253575 A1 | 8/2021 | Dey et al. |
| 2021/0300924 A1 | 9/2021 | Liu et al. |
| 2021/0300947 A1 | 9/2021 | Dey et al. |
| 2021/0323977 A1 | 10/2021 | Liu et al. |
| 2021/0355122 A1 | 11/2021 | Dey et al. |
| 2021/0395239 A1 | 12/2021 | Dey et al. |
| 2022/0112187 A1 | 4/2022 | Liu et al. |
| 2022/0363665 A1 | 11/2022 | Dey et al. |
| 2023/0002415 A1 | 5/2023 | Chen et al. |

FOREIGN PATENT DOCUMENTS

| | | |
|---|---|---|
| WO | 2015/057655 A1 | 4/2015 |
| WO | 2015/057659 A1 | 4/2015 |
| WO | 2019/028302 A1 | 2/2017 |
| WO | 2017/106607 A1 | 6/2017 |
| WO | 2018/005586 A1 | 1/2018 |
| WO | 2018/026620 A1 | 2/2018 |
| WO | 2018/031434 A1 | 2/2018 |
| WO | 2018/047081 A1 | 3/2018 |
| WO | 2018/049089 A1 | 3/2018 |

(Continued)

OTHER PUBLICATIONS

Chichester, T. How To Prevent Lupus. Health.com. 2023. Web. pp. 1-8. (Year: 2023).*
Alper, P., et al., "Discovery of potent, orally bioavailable in vivo efficacious antagonists of the TLR7/8 pathway" Bioorg Med Chem Lett 30(17):127366 (1-5) (Sep. 1, 2020).
"International Preliminary Report on Patentability—PCT/EP2018/073929" (Report Issuance Date: Mar. 9, 2021, Chapter I), :pp. 1-7 (Mar. 18, 2021).
"International Search Report—PCT/EP2018/073929" (w/Written Opinion), :pp. 1-12 (Oct. 25, 2018).

(Continued)

*Primary Examiner* — Eric Olson
*Assistant Examiner* — Samuel L Galster
(74) *Attorney, Agent, or Firm* — Bradley E. Davis

(57) ABSTRACT

The present invention relates to compounds of formula (I), wherein $R^1$, $R^2$, $R^3$ and $R^4$ are as described herein, and their pharmaceutically acceptable salt, enantiomer or diastereomer thereof, and compositions including the compounds and methods of using the compounds.

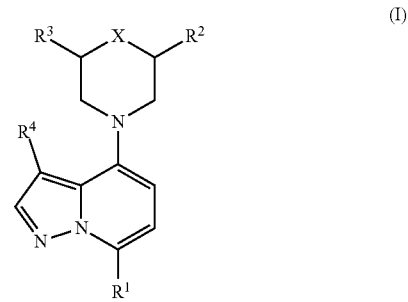

17 Claims, No Drawings

(56) References Cited

FOREIGN PATENT DOCUMENTS

| | | |
|---|---|---|
| WO | 2019/018354 A1 | 1/2019 |
| WO | 2019/028301 A1 | 2/2019 |
| WO | 2019/099336 A1 | 5/2019 |
| WO | 2019/118799 A1 | 6/2019 |
| WO | 2019/123294 A2 | 6/2019 |
| WO | 2019/125849 A1 | 6/2019 |
| WO | 2019/126081 A1 | 6/2019 |
| WO | 2019/126082 A1 | 6/2019 |
| WO | 2019/126083 A1 | 6/2019 |
| WO | 2019/126113 A1 | 6/2019 |
| WO | 2019/126242 A1 | 6/2019 |
| WO | 2019/126253 A1 | 6/2019 |
| WO | 2019/220390 A1 | 11/2019 |
| WO | 2019/238616 A1 | 12/2019 |
| WO | 2019/238629 A1 | 12/2019 |
| WO | 2020/064792 A1 | 2/2020 |
| WO | 2020/052738 A1 | 3/2020 |
| WO | 2020/043271 A1 | 5/2020 |
| WO | 2020/094749 A1 | 5/2020 |
| WO | 2020/048583 A1 | 12/2020 |
| WO | 2020/048595 A1 | 12/2020 |
| WO | 2020/048596 A1 | 12/2020 |
| WO | 2020/048605 A1 | 12/2020 |
| WO | 2021/048200 A1 | 3/2021 |
| WO | 2021/052892 A1 | 3/2021 |
| WO | 2021/099406 A1 | 5/2021 |

OTHER PUBLICATIONS

Knoepfel, T., et al., "Target-Based Identification and Optimization of 5-Indazol-5-yl Pyridones as Toll-like Receptor 7 and 8 Antagonists Using a Biochemical TLR8 Antagonist Competition Assay" J Med Chem 63(15):8276-8295 (Jul. 30, 2020).

Mussari, C., et al., "Discovery of Potent and Orally Bioavailable Small Molecule Antagonists of Toll-like Receptors 7/8/9 (TLR7/8/9)" ACS Med Chem Lett 11(9):1751-1758 (Jul. 29, 2020).

International Preliminary Report on Patentability—PCT/EP2019/065091 issued on Dec. 15, 2020, pp. 1-9.

International Preliminary Report on Patentability—PCT/EP2020/082567 issued May 17, 2022, pp. 1-7.

International Search Report for PCT/EP2019/065091 mailed on Aug. 19, 2019, pp. 1-13.

International Search Report with Written Opinion—PCT/EP2020/082567 mailed Jan. 19, 2021, pp. 1-12.

\* cited by examiner

PYRAZOLOPYRIDINE COMPOUNDS FOR THE TREATMENT OF AUTOIMMUNE DISEASE

The present invention relates to organic compounds useful for therapy and/or prophylaxis in a mammal, and in particular to antagonist of TLR7 and/or TLR8 and/or TLR9 useful for treating systemic lupus erythematosus or lupus nephritis.

FIELD OF THE INVENTION

Autoimmune connective tissue disease (CTD) include prototypical autoimmune syndromes such as Systemic Lupus Erythematosus (SLE), primary Sjögren's syndrome (pSjS), mixed connective tissue disease (MCTD), Dermatomyositis/Polymyositis (DM/PM), Rheumatoid Arthritis (RA), and systemic sclerosis (SSc). With the exception of RA, no really effective and safe therapies are available to patients. SLE represents the prototypical CTD with a prevalence of 20-150 per 100,000 and causes broad inflammation and tissue damage in distinct organs, from commonly observed symptoms in the skin and joints to renal, lung, or heart failure. Traditionally, SLE has been treated with non-specific anti-inflammatory or immunosuppressive drugs. However, long term usage of immunosuppressive drug, e.g. corticosteroids is only partially effective, and is associated with undesirable toxicity and side effects. Belimumab is the only FDA-approved drug for lupus in the last 50 years, despite its modest and delayed efficacy in only a fraction of SLE patients (Navarra, S. V. et al *Lancet* 2011, 377, 721.). Other biologics, such as anti-CD20 mAbs, mAbs against or soluble receptors of specific cytokines, have failed in most clinical studies. Thus, novel therapies are required that provide sustained improvement in a greater proportion of patient groups and are safer for chronic use in many autoimmune as well as auto-inflammation diseases.

Toll Like Receptors (TLR) are an important family of pattern recognition receptors (PRR) which can initiate broad immune responses in a wide variety of immune cells. As natural host defense sensors, endosomal TLRs 7, 8 and 9 recognize nucleic acids derived from viruses, bacteria; specifically, TLR7/8 and TLR9 recognize single-stranded RNA (ssRNA) and single-stranded CpG-DNA, respectively. However, aberrant nucleic acid sensing of TRL7/8/9 is considered as a key node in a broad of autoimmune and auto-inflammatory diseases (Krieg, A. M. et al. *Immunol. Rev.* 2007, 220, 251. Jiménez-Dalmaroni, M. J. et al *Autoimmun Rev.* 2016, 15, 1. Chen, J. Q., et al. *Clinical Reviews in Allergy & Immunology* 2016, 50, 1.) Therefore, TLR7/8/9 represents a new therapeutic target for autoimmune and auto-inflammatory diseases, for which no effective steroid-free and non-cytotoxic oral drugs exist, and inhibition of these pathways from the very upstream may deliver satisfying therapeutic effects. From a safety perspective, because there are multiple nucleic acid sensing pathways (e.g. other TLRs, cGAS/STING), such redundancy should still allow responses to infection in the presence of TLR7/8/9 inhibition. As such, we proposed and invented oral compounds that target and suppress TLR7/8/9 for the treatment of autoimmune and auto-inflammatory diseases.

SUMMARY OF THE INVENTION

The present invention relates to novel compounds of formula (I),

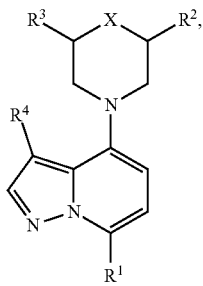

wherein
$R^1$ is cyano, $C_{1-6}$alkyl, halogen, halo$C_{1-6}$alkyl or nitro;
$R^2$ is $C_{1-6}$alkyl or halo$C_{1-6}$alkyl;
$R^3$ is $-NHR^{3a}$ or $-COR^{3b}$, wherein
  $R^{3a}$ is H, amino$C_{1-6}$alkylcarbonyl, $(C_{1-6}alkyl)_2$amino$C_{1-6}$alkylcarbonyl or cyano$C_{1-6}$alkyl;
  $R^{3b}$ is (heterocyclylcarbonyl)phenylamino, (hydroxy$C_{1-6}$alkoxy)$C_{1-6}$alkylamino, adamantylamino, amino$C_{1-6}$alkylamino, $C_{1-6}$alkoxy$C_{1-6}$alkylamino, $C_{1-6}$alkylamino, $C_{1-6}$alkylpyrazolylamino, cyano$C_{3-7}$cycloalkylamino, heterocyclyl, heterocyclylamino, heterocyclyl$C_{1-6}$alkylamino, hydroxy$C_{1-6}$alkylamino, hydroxy$C_{1-6}$alkyl$C_{3-7}$cycloalkylamino, hydroxy$C_{3-7}$cycloalkylamino or pyridylamino;
$R^4$ is H or halogen;
X is O or $CH_2$;
or a pharmaceutically acceptable salt, enantiomer or diastereomer thereof.

Another object of the present invention is related to novel compounds of formula (I), their manufacture, medicaments based on a compound in accordance with the invention and their production as well as the use of compounds of formula (I) as TLR7 and/or TLR8 and/or TLR9 antagonist, and for the treatment or prophylaxis of systemic lupus erythematosus or lupus nephritis. The compounds of formula (I) show superior TLR7 and/or TLR8 and/or TLR9 antagonism activity. In addition, the compounds of formula (I) also show good cytotoxicity, solubility, human microsome stability and SDPK profiles, as well as low CYP inhibition.

DETAILED DESCRIPTION OF THE INVENTION

Definitions

The term "$C_{1-6}$alkyl" denotes a saturated, linear or branched chain alkyl group containing 1 to 6, particularly 1 to 4 carbon atoms, for example methyl, ethyl, n-propyl, isopropyl, n-butyl, isobutyl, tert-butyl and the like. Particular "$C_{1-6}$alkyl" groups are methyl, ethyl and n-propyl.

The term "$C_{2-6}$alkynyl" denotes a saturated, linear or branched chain alkynyl group containing 1 to 6, particularly 1 to 4 carbon atoms, for example ethynyl, propynyl and the like. Particular "$C_{1-6}$alkyl" group is ethynyl.

The term "halogen" and "halo" are used interchangeably herein and denote fluoro, chloro, bromo, or iodo.

The term "halo$C_{1-6}$alkyl" denotes an alkyl group wherein at least one of the hydrogen atoms of the alkyl group has been replaced by same or different halogen atoms, particularly fluoro atoms. Examples of halo$C_{1-6}$alkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, difluoromethyl, trifluoromethyl and trifluoroethyl.

The term "$C_{3-7}$cycloalkyl" denotes a saturated monocyclic or bicyclic carbon ring containing from 3 to 7 carbon atoms, particularly from 3 to 6 carbon atoms, for example, cyclopropyl, cyclobutyl, cyclopentyl, cyclohexyl, cycloheptyl, bicyclo[1.1.1]pentanyl and the like. Particular "$C_{3-7}$ cycloalkyl" groups are cyclopropyl, cyclohexyl and bicyclo [1.1.1]pentanyl.

The term "halopiperidinyl" denotes a piperidinyl group wherein at least one of the hydrogen atoms of the piperidinyl group has been replaced by same or different halogen atoms, particularly fluoro atoms. Examples of halopiperidinyl include fluoropyrrolidinyl and difluoropiperidinyl.

The term "halopyrrolidinyl" denotes a pyrrolidinyl group wherein at least one of the hydrogen atoms of the pyrrolidinyl group has been replaced by same or different halogen atoms, particularly fluoro atoms. Examples of halopiperidinyl include fluoropyrrolidinyl and difluoropyrrolidinyl.

The term "heterocyclyl" denotes a monovalent saturated or partly unsaturated mono- or bicyclic ring system of 3 to 12 ring atoms, comprising 1, 2, or 3 ring heteroatoms selected from N, O and S, the remaining ring atoms being carbon. In particular embodiments, heterocyclyl is a monovalent saturated monocyclic ring system of 4 to 10 ring atoms, comprising 1, 2, or 3 ring heteroatoms selected from N, O and S, the remaining ring atoms being carbon. Examples for monocyclic saturated heterocyclyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Heterocyclyl can be fully or partially saturated. Examples for bicyclic saturated heterocyclyl are azabicyclo[2.2.1]heptanyl, azabicyclo[3.1.0]hexanyl, azabicyclo[3.2.1]octanyl, azabicyclo[3.3.1]nonanyl, azaspiro[3.3]heptanyl, azabicyclo[2.2.2]octanyl, azaspiro[2.4]heptanyl, diazaspiro[5.5]undecanyl and oxaazabicyclo[3.3.1]nonanyl. Examples for partially saturated heterocyclyl are dihydrofuryl, imidazolinyl, dihydro-oxazolyl, tetrahydropyridinyl, and dihydropyranyl. Monocyclic or bicyclic heterocyclyl can be further substituted by halogen, hydroxy, amino, $C_{1-6}$alkyl, halo$C_{1-6}$alkyl or heterocyclyl.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "A pharmaceutically active metabolite" denotes a pharmacologically active product produced through metabolism in the body of a specified compound or salt thereof. After entry into the body, most drugs are substrates for chemical reactions that may change their physical properties and biologic effects. These metabolic conversions, which usually affect the polarity of the compounds of the invention, alter the way in which drugs are distributed in and excreted from the body. However, in some cases, metabolism of a drug is required for therapeutic effect.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "pharmaceutical composition" denotes a mixture or solution comprising a therapeutically effective amount of an active pharmaceutical ingredient together with pharmaceutically acceptable excipients to be administered to a mammal, e.g., a human in need thereof.

Antagonist of TLR7 and/or TLR8 and/or TLR9

The present invention relates to a compound of formula (I),

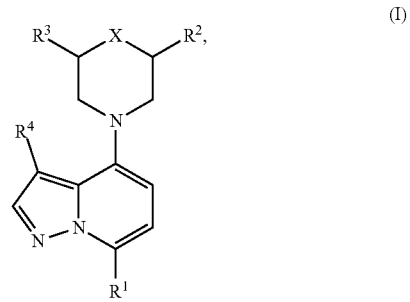

wherein
R¹ is cyano, $C_{1-6}$alkyl, halogen, halo$C_{1-6}$alkyl or nitro;
R² is $C_{1-6}$alkyl or halo$C_{1-6}$alkyl;
R³ is —NHR$^{3a}$ or —COR$^{3b}$, wherein
R$^{3a}$ is H, amino$C_{1-6}$alkylcarbonyl, ($C_{1-6}$alkyl)$_2$amino$C_{1-6}$alkylcarbonyl or cyano$C_{1-6}$alkyl;
R$^{3b}$ is (heterocyclylcarbonyl)phenylamino, (hydroxy$C_{1-6}$alkoxy)$C_{1-6}$alkylamino, adamantylamino, amino$C_{1-6}$alkylamino, $C_{1-6}$alkoxy$C_{1-6}$alkylamino, $C_{1-6}$alkylamino, $C_{1-6}$alkylpyrazolylamino, cyano$C_{3-7}$cycloalkylamino, heterocyclyl, heterocyclylamino, heterocyclyl$C_{1-6}$alkylamino, hydroxy$C_{1-6}$alkylamino, hydroxy$C_{1-6}$alkyl$C_{3-7}$cycloalkylamino, hydroxy$C_{3-7}$cycloalkylamino or pyridylamino;
R⁴ is H or halogen;
X is O or CH₂;
or a pharmaceutically acceptable salt, enantiomer or diastereomer thereof.

A further embodiment of present invention is (ii) a compound of formula (I) according to (i), wherein R¹ is cyano or halogen.

A further embodiment of present invention is (iii) a compound of formula (I) according to (ii), wherein
R¹ is cyano or halogen;
R² is $C_{1-6}$alkyl;
R³ is —NHR$^{3a}$ or —COR$^{3b}$, wherein
R$^{3a}$ is H, amino$C_{1-6}$alkylcarbonyl, ($C_{1-6}$alkyl)$_2$amino$C_{1-6}$alkylcarbonyl or cyano$C_{1-6}$alkyl;
R$^{3b}$ is ($C_{1-6}$alkylmorpholinyl)$C_{1-6}$alkylamino, (hydroxy$C_{1-6}$alkoxy)$C_{1-6}$alkylamino, (piperazinylcarbonyl)phenylamino, adamantylamino, aminoazetidinyl, amino$C_{1-6}$alkylamino, azabicyclo[2.2.1]heptanylamino, azabicyclo[3.1.0]hexanylamino, azabicyclo[3.2.1]octanylamino, azabicyclo[3.3.1]nonanylamino, azaspiro[3.3]heptanylamino, azepanylamino, $C_{1-6}$alkoxy$C_{1-6}$alkylamino, $C_{1-6}$alkylamino, $C_{1-6}$alkylazabicyclo[2.2.2]octanylamino, $C_{1-6}$alkylazabicyclo[3.2.1]octanylamino, $C_{1-6}$alkylazabicyclo[3.3.1]nonanylamino, $C_{1-6}$alkylazaspiro[2.4]heptanylamino, $C_{1-6}$alkylpiperidylamino, $C_{1-6}$alkylpyrazolylamino, cyano$C_{3-7}$cycloalkylamino, diazaspiro[5.5]undecanyl, halopyrrolidinylamino, halopyrrolidinyl$C_{1-6}$alkylamino, hydroxy$C_{1-6}$alkylamino, hydroxy$C_{1-6}$alkyl$C_{3-7}$cycloalkylamino, hydroxy$C_{3-7}$cycloalkylamino, oxaazabicyclo[3.3.1]nonanylamino, piperidylamino, pyridylamino, pyrrolidinylamino, pyrrolidinyl$C_{1-6}$alkylamino or tetrahydropyranylamino;
R⁴ is H or halogen;
X is O or CH₂;
or a pharmaceutically acceptable salt, enantiomer or diastereomer thereof.

A further embodiment of present invention is (iv) a compound of formula (I) according to (iii), wherein R¹ is cyano or chloro.

A further embodiment of present invention is (v) a compound of formula (I) according to (iv), wherein R¹ is cyano.

A further embodiment of present invention is (vi) a compound of formula (I) according to (iv) or (v), wherein R² is methyl.

A further embodiment of present invention is (vii) a compound of formula (I) according to any one of (iii) to (vi), wherein R³ is —NHR$^{3a}$ or —COR$^{3b}$, wherein R$^{3a}$ is H, aminoethylcarbonyl, (dimethylamino)methylcarbonyl or cyanomethyl; R$^{3b}$ is (hydroxyethoxy)ethylamino, (hydroxymethyl)bicyclo[1.1.1]pentanylamino, (methylmorpholinyl)methylamino, (piperazinylcarbonyl)phenylamino, 2-azabicyclo[2.2.1]heptan-5-ylamino, 2-azaspiro[3.3]heptan-6-ylamino, 2-methyl-2-azabicyclo[2.2.2]octan-5-ylamino, 3,9-diazaspiro[5.5]undecanyl, 3-azabicyclo[3.1.0]hexan-6-ylamino, 3-azabicyclo[3.2.1]octan-8-ylamino, 3-azabicyclo[3.3.1]nonan-9-ylamino, 3-oxa-7-azabicyclo[3.3.1]nonan-9-ylamino, 3-oxa-9-azabicyclo[3.3.1]nonan-7-ylamino, 5-methyl-5-azaspiro[2.4]heptan-7-ylamino, 8-azabicyclo[3.2.1]octan-3-ylamino, 8-methyl-8-azabicyclo[3.2.1]octan-3-ylamino, 9-azabicyclo[3.3.1]nonan-3-ylamino, 9-methyl-9-azabicyclo[3.3.1]nonan-3-ylamino, adamantylamino, aminoazetidinyl, amino dimethylethylamino, amino dimethylpropylamino, azepan-4-ylamino, cyanocyclopropylamino, difluoropyrrolidinylmethylamino, dimethylpropylamino, fluoropyrrolidinylamino, hydroxybutylamino, hydroxycyclohexylamino, hydroxydimethylethylamino, methoxyethylamino, methylpiperidylamino, methylpyrazolylamino, piperidylamino, pyridylamino, pyrrolidinylamino, pyrrolidinylmethylamino or tetrahydropyranylamino.

A further embodiment of present invention is (viii) a compound of formula (I) according to any one of (i) to (vii), wherein R³ is —COR$^{3b}$, wherein R$^{3b}$ is methylpiperidylamino, azepanylamino or 3-azabicyclo[3.3.1]nonan-9-ylamino.

A further embodiment of present invention is (ix) a compound of formula (I) according to (viii), wherein R⁴ is H or fluoro.

A further embodiment of present invention is (x) a compound of formula (I) according to (xi), wherein X is O.

Another embodiment of present invention is that (xi) particular compounds of formula (I) are the following:
(2R,6R)-4-(7-cyanopyrazolo[1,5-a]pyridin-4-yl)-6-methyl-N-(1-methyl-4-piperidyl)morpholine-2-carboxamide;
(2R,6R)-4-(7-cyanopyrazolo[1,5-a]pyridin-4-yl)-N-[(3S,4R)-4-fluoropyrrolidin-3-yl]-6-methyl-morpholine-2-carboxamide;
(2R,6R)-N-(2-azaspiro[3.3]heptan-6-yl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-6-methyl-N-tetrahydropyran-4-yl-morpholine-2-carboxamide;
Cis-(2R,6R)-4-(7-cyanopyrazolo[1,5-a]pyridin-4-yl)-6-methyl-N-(4-fluoropyrrolidin-3-yl) morpholine-2-carboxamide;
(2R,6R)-N-(azepan-4-yl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-6-methyl-N-[(4-methylmorpholin-2-yl)methyl]morpholine-2-carboxamide;
4-[(2R,6R)-2-(3-aminoazetidine-1-carbonyl)-6-methyl-morpholin-4-yl]pyrazolo[1,5a]pyridine-7-carbonitrile;
(2R,6R)-4-(7-cyanopyrazolo[1,5-a]pyridin-4-yl)-N-(2-methoxyethyl)-6-methyl-morpholine-2-carboxamide;
(2R,6R)-4-(7-cyanopyrazolo[1,5-a]pyridin-4-yl)-N-[2-(2-hydroxyethoxy)ethyl]-6-methyl-morpholine-2-carboxamide;
(2R,6R)-N-(1-cyanocyclopropyl)-4-(7-cyanopyrazolo[1,5-a]pyridin-4-yl)-6-methyl-morpholine-2-carboxamide;
(2R,6R)-N-(1-adamantyl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-N-(2-hydroxybutyl)-6-methyl-morpholine-2-carboxamide;
(2R,6R)-N-(9-azabicyclo[3.3.1]nonan-3-yl)-4-(7-cyanopyrazolo[1,5-a]pyridin-4-yl)-6-methyl-morpholine-2-carboxamide;

(2R,6R)-4-(7-cyanopyrazolo[1,5-a]pyridin-4-yl)-N-[3-(hydroxymethyl)-1-bicyclo[1.1.1]pentanyl]-6-methyl-morpholine-2-carboxamide;

(2R,6R)-4-(7-cyanopyrazolo[1,5-a]pyridin-4-yl)-N-(2-hydroxy-1,1-dimethyl-ethyl)-6-methyl-morpholine-2-carboxamide;

(2R,6R)-4-(7-cyanopyrazolo[1,5-a]pyridin-4-yl)-N-(1,1-dimethylpropyl)-6-methyl-morpholine-2-carboxamide;

(2R,6R)-4-(7-cyanopyrazolo[1,5-a]pyridin-4-yl)-N-[(4,4-difluoropyrrolidin-3-yl)methyl]-6-methyl-morpholine-2-carboxamide;

(2R,6R)-4-(7-cyanopyrazolo[1,5-a]pyridin-4-yl)-6-methyl-N-(4-methyl-4-piperidyl)morpholine-2-carboxamide;

Cis-(2R,6R)-4-(7-cyanopyrazolo[1,5-a]pyridin-4-yl)-N-(4-hydroxycyclohexyl)-6-methyl-morpholine-2-carboxamide;

Trans-(2R,6R)-4-(7-cyanopyrazolo[1,5-a]pyridin-4-yl)-N-(4-hydroxycyclohexyl)-6-methyl-morpholine-2-carboxamide;

Endo-(2R,6R)-4-(7-cyanopyrazolo[1,5-a]pyridin-4-yl)-6-methyl-N-[3-oxa-9-azabicyclo[3.3.1]nonan-7-yl]morpholine-2-carboxamide;

Exo-(2R,6R)-N-[8-azabicyclo[3.2.1]octan-3-yl]-4-(7-cyanopyrazolo[1,5-a]pyridin-4-yl)-6-methyl-morpholine-2-carboxamide;

(2R,6R)-4-(7-cyanopyrazolo[1,5-a]pyridin-4-yl)-6-methyl-N-(4-piperidyl)morpholine-2-carboxamide;

(2R,6R)-4-(7-cyanopyrazolo[1,5-a]pyridin-4-yl)-6-methyl-N-pyrrolidin-3-yl-morpholine-2-carboxamide; (2R,6R)-N-(3-azabicyclo[3.2.1]octan-8-yl)-4-(7-cyanopyrazolo[1,5-a]pyridin-4-yl)-6-methyl-morpholine-2-carboxamide;

(2R,6R)-4-(7-cyanopyrazolo[1,5-a]pyridin-4-yl)-6-methyl-N-(3-oxa-7-azabicyclo[3.3.1]nonan-9-yl)morpholine-2-carboxamide;

4-[(2R,6R)-2-(3,9-diazaspiro[5.5]undecane-3-carbonyl)-6-methyl-morpholin-4-yl]pyrazolo[1,5-a]pyridine-7-carbonitrile;

(2R,6R)-4-(7-cyanopyrazolo[1,5-a]pyridin-4-yl)-6-methyl-N-(4-pyridyl)morpholine-2-carboxamide;

(2R,6R)-4-(7-cyanopyrazolo[1,5-a]pyridin-4-yl)-6-methyl-N-(1-methylpyrazol-3-yl)morpholine-2-carboxamide;

Trans-(2R,6R)-N-(3-azabicyclo[3.1.0]hexan-6-yl)-4-(7-cyanopyrazolo[1,5-a]pyridin-4-yl)-6-methyl-morpholine-2-carboxamide;

(2R,6R)-4-(7-cyanopyrazolo[1,5-a]pyridin-4-yl)-6-methyl-N-(5-methyl-5-azaspiro[2.4]heptan-7-yl)morpholine-2-carboxamide;

(2R,6R)-4-(7-cyanopyrazolo[1,5-a]pyridin-4-yl)-6-methyl-N-(8-methyl-8-azabicyclo[3.2.1]octan-3-yl)morpholine-2-carboxamide;

(2R,6R)-4-(7-cyanopyrazolo[1,5-a]pyridin-4-yl)-6-methyl-N-(2-methyl-2-azabicyclo[2.2.2]octan-5-yl)morpholine-2-carboxamide;

(2R,6R)-4-(7-cyanopyrazolo[1,5-a]pyridin-4-yl)-6-methyl-N-(9-methyl-9-azabicyclo[3.3.1]nonan-3-yl)morpholine-2-carboxamide;

(2R,6R)-N-(2-azabicyclo[2.2.1]heptan-5-yl)-4-(7-cyanopyrazolo[1,5-a]pyridin-4-yl)-6-methyl-morpholine-2-carboxamide;

(2R,6R)-N-(3-azabicyclo[3.3.1]nonan-9-yl)-4-(7-cyanopyrazolo[1,5-a]pyridin-4-yl)-6-methyl-morpholine-2-carboxamide;

(2R,6R)-4-(7-chloropyrazolo[1,5-a]pyridin-4-yl)-6-methyl-N-(1-methyl-4-piperidyl)morpholine-2-carboxamide;

(2R,6R)-N-(3-amino-2,2-dimethyl-propyl)-4-(7-cyanopyrazolo[1,5-a]pyridin-4-yl)-6-methyl-morpholine-2-carboxamide;

(2R,6R)-4-(7-cyanopyrazolo[1,5-a]pyridin-4-yl)-6-methyl-N-(pyrrolidin-3-ylmethyl)morpholine-2-carboxamide;

(2R,6R)-N-(2-amino-1,1-dimethyl-ethyl)-4-(7-cyanopyrazolo[1,5-a]pyridin-4-yl)-6-methyl-morpholine-2-carboxamide;

(2R,6R)-4-(7-cyanopyrazolo[1,5-a]pyridin-4-yl)-6-methyl-N-[4-(piperazine-1-carbonyl)phenyl]morpholine-2-carboxamide;

4-[(3R,5S)-3-amino-5-methyl-1-piperidyl]pyrazolo[1,5-a]pyridine-7-carbonitrile;

(2S)-2-amino-N-[(3R,5S)-1-(7-cyanopyrazolo[1,5-a]pyridin-4-yl)-5-methyl-3-piperidyl]propanamide;

N-[(3R,5S)-1-(7-cyanopyrazolo[1,5-a]pyridin-4-yl)-5-methyl-3-piperidyl]-2-(dimethylamino)acetamide;

4-[(3R,5 S)-3-(cyanomethylamino)-5-methyl-1-piperidyl]pyrazolo[1,5-a]pyridine-7-carbonitrile; and (2R,6R)-4-(7-cyan-3-fluoro-pyrazolo[1,5-a]pyridin-4-yl)-6-methyl-N-(1-methyl-4-piperidyl)morpholine-2-carboxamide;

or a pharmaceutically acceptable salt, enantiomer or diastereomer thereof.

Synthesis

The compounds of the present invention can be prepared by any conventional means. Suitable processes for synthesizing these compounds as well as their starting materials are provided in the schemes below and in the examples. All substituents, in particular, $R^1$ to R4 are as defined above unless otherwise indicated. Specifically, in the schemes below, $R^3$ assumes the definition for $R^2$ in Structure (I) hereinabove. Furthermore, and unless explicitly otherwise stated, all reactions, reaction conditions, abbreviations and symbols have the meanings well known to a person of ordinary skill in organic chemistry.

General synthetic route for preparing the compound of formula (I) is shown below.

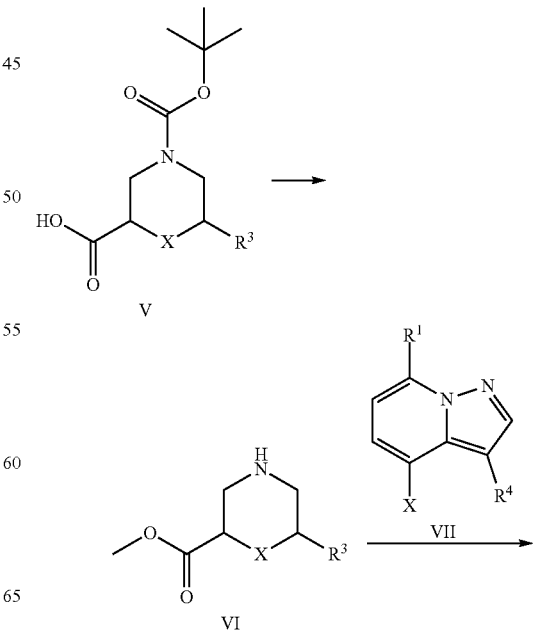

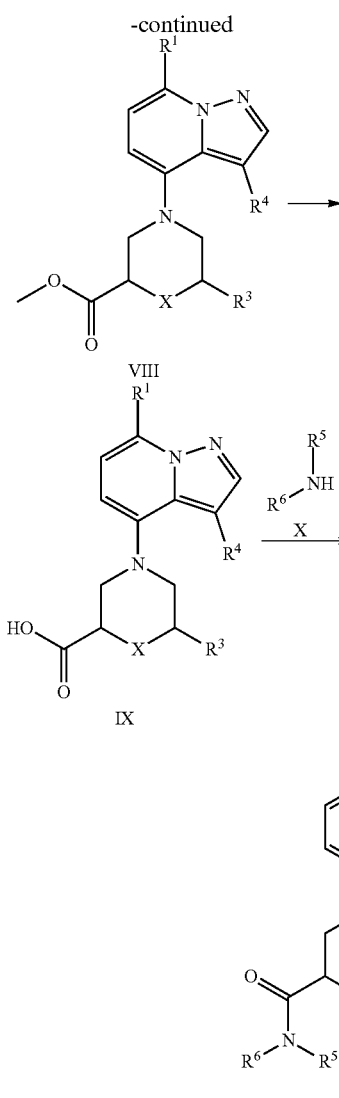

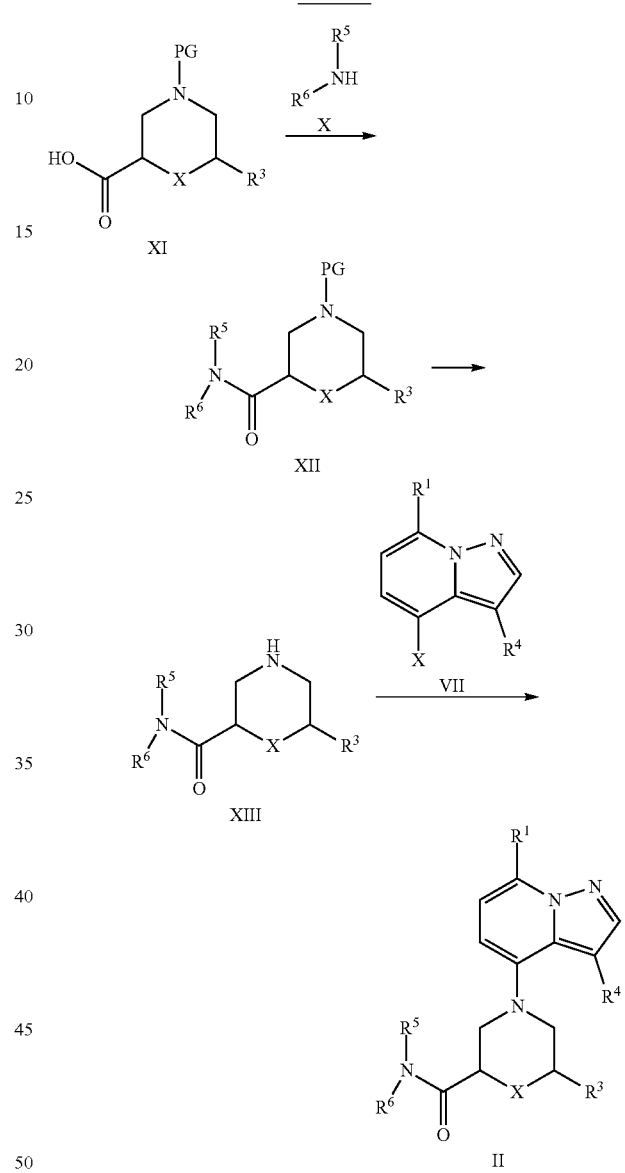

wherein $R^5$ and $R^6$ are independently selected from H, (hydroxyC$_{1-6}$alkoxy)C$_{1-6}$alkyl, adamantly, amino C$_{1-6}$alkyl, C$_{1-6}$alkoxyC$_{1-6}$alkyl, C$_{1-6}$alkyl, C$_{1-6}$alkylpyrazolyl, cyanoC$_{3-7}$cycloalkyl, hydroxyC$_{1-6}$alkyl, hydroxyC$_{1-6}$alkylC$_{3-7}$cycloalkyl, pyridyl, hydroxyC$_{3-7}$cycloalkyl, heterocyclylC$_{1-6}$alkyl, (heterocyclylcarbonyl)phenyl or heterocyclyl; or $R^5$ and $R^6$ together with the nitrogen they are attached to form a heterocyclyl.

The starting material carboxylic acid (V) can be converted to ester (V) via esterification with MeOH. The subsequent coupling of halide (VII) with compound of formula (VI) can be achieved by direct coupling in the presence of a base, such as DIPEA and K$_2$CO$_3$, or under Buchwald-Hartwig amination conditions (ref: *Acc. Chem. Res.* 1998, 31, 805-818; Chem. Rev. 2016, 116, 12564-12649; *Topics in Current Chemistry*, 2002, 219, 131-209; and references cited therein) with a catalyst, such as Ruphos Pd-G2, and a base, such as Cs$_2$CO$_3$, to provide compound of formula (VIII). Hydrolysis of compound of formula (VIII) in basic condition, such as LiOH in THF/water, gives carboxylic acid (IX), which is condensed with amine (X) in the presence of a coupling reagent, such as HATU, to give the compound of formula (II). In some embodiment, the coupling of compound of formula (IX) and amine (X) may give a product containing a protecting group, e.g. Boc, originated from amine (X), which will be removed before affording the final compound of formula (II).

wherein PG is a protecting group, such as Boc and Cbz. $R^5$ and $R^6$ are defined as above.

The carboxylic acid (XI) can be condensed with amine (X) in the presence of a coupling reagent, such as HATU, to give compound of formula (XII). The protecting group of compound of formula (XII), e.g. Boc or Cbz, can be removed under acidic condition, such as TFA/CH$_2$Cl$_2$ and HCl in dioxane, or under hydrogenation condition (e.g. Pd—C, H$_2$), to give compound of formula (XIII). Coupling of compound of formula (XIII) with the halide (VII) under the Buchwald-Hartwig amination condition with a catalyst, such as Ruphos Pd-G2, and a base, such as Cs$_2$CO$_3$, affords the compounds of formula (II). In some embodiment, the coupling of halide (VII) and compound of formula (XIII) may give a product containing a protecting group, e.g. Boc, originated from amine (X), which will be removed before affording the final compound of formula (II).

Scheme 3

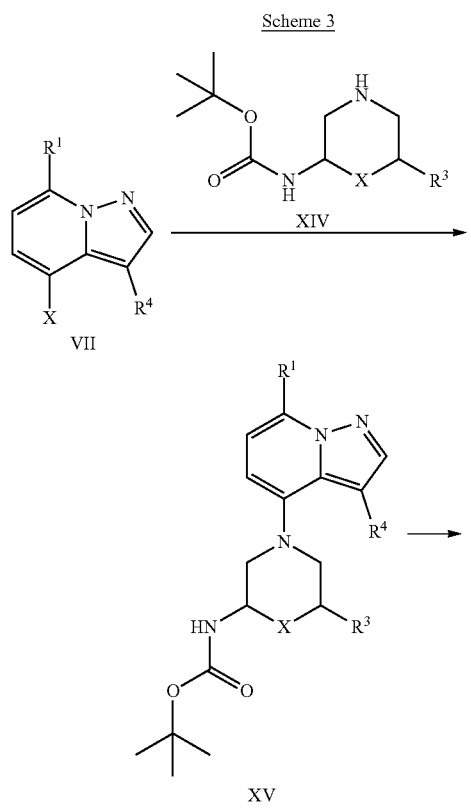

wherein $R^7$ is H, $C_{1-6}$alkyl, amino$C_{1-6}$alkyl, $(C_{1-6}alkyl)_2$amino$C_{1-6}$alkyl or heterocyclyl.

The synthesis of the compound of formula (III) can be achieved by the coupling of halide (VII) with amine (XIV) in the presence of a base, such as DIPEA and $K_2CO_3$, or under Buchwald-Hartwig amination conditions with a catalyst, such as Ruphos Pd-G2, and a base, such as $Cs_2CO_3$, to give compound of formula (XV). Compound of formula (XV) is deprotected under an acidic condition, such as $TFA/CH_2Cl_2$ or HCl in dioxane, to afford the final compound of formula (III). Compound of formula (III) can be further coupled with carboxylic acid (XVI) in the presence of a coupling reagent, such as HATU, to give compound of formula (IV). In some embodiment, the coupling of compound of formula (III) and carboxylic acid (XVI) may give a product containing a protecting group, e.g. Boc, originated from carboxylic acid (XVI), which will be removed before affording the final compound of formula (IV).

This invention also relates to a process for the preparation of a compound of formula (I) comprising any of the following steps:

a) the reaction of compound of formula (IX),

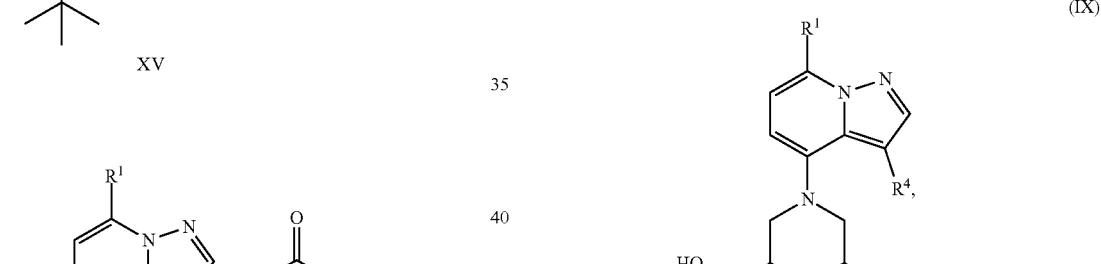

with amine (X) in the presence of a coupling reagent;

b) the reaction of compound of formula (XII),

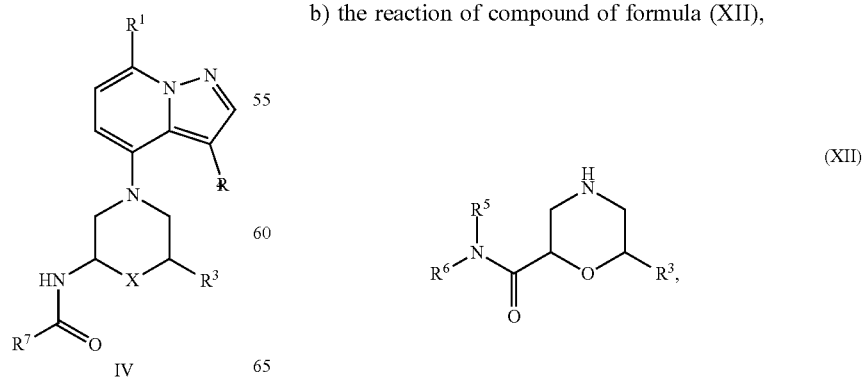

with compound of formula (VII) in the presence of a catalyst and a base;

c) the reaction of compound of formula (XV),

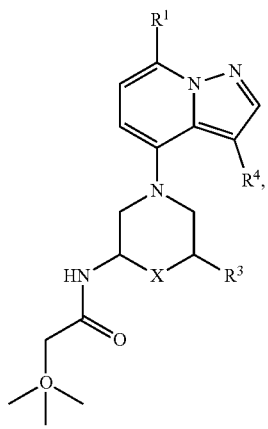

(XV)

in the presence of an acid;
d) the reaction of compound of formula (III),

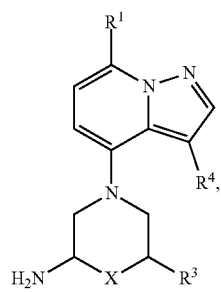

(III)

with an acid (XVI) in the presence of a coupling reagent;

In step a) and d) the coupling reagent can be for example HATU.

In step b), the catalyst can be for example Ruphos Pd-G2, the base can be for example $Cs_2CO_3$.

In step c), the acid can be for example $TFA/CH_2Cl_2$ and HCl in dioxane.

A compound of formula (I), (II) (III) or (IV) when manufactured according to the above process is also an object of the invention.

Compounds of this invention can be obtained as mixtures of diastereomers or enantiomers, which can be separated by methods well known in the art, e.g. (chiral) HPLC or SFC.

Indications and Methods of Treatment

The present invention provides compounds that can be used as TLR7 and/or TLR8 and/or TLR9 antagonist, which inhibits pathway activation through TLR7 and/or TLR8 and/or TLR9 as well as respective downstream biological events including, but not limited to, innate and adaptive immune responses mediated through the production of all types of cytokines and all forms of auto-antibodies. Accordingly, the compounds of the invention are useful for blocking TLR7 and/or TLR8 and/or TLR9 in all types of cells that express such receptor(s) including, but not limited to, plasmacytoid dendritic cell, B cell, T cell, macrophage, monocyte, neutrophil, keratinocyte, epithelial cell. As such, the compounds can be used as a therapeutic or prophylactic agent for systemic lupus erythematosus and lupus nephritis.

The present invention provides methods for treatment or prophylaxis of systemic lupus erythematosus and lupus nephritis in a patient in need thereof.

Another embodiment includes a method of treating or preventing systemic lupus erythematosus and lupus nephritis in a mammal in need of such treatment, wherein the method comprises administering to said mammal a therapeutically effective amount of a compound of formula (I), a stereoisomer, tautomer, prodrug or pharmaceutically acceptable salt thereof.

EXAMPLES

The invention will be more fully understood by reference to the following examples. They should not, however, be construed as limiting the scope of the invention.

Abbreviations

The invention will be more fully understood by reference to the following examples. They should not, however, be construed as limiting the scope of the invention.

Abbreviations used herein are as follows:
ACN: acetonitrile
DIPEA: N,N-diisopropylethylamine
EtOAc: ethyl acetate
FA: formic acid
HATU: 1-[Bis(dimethylamino)methylene]-1H-1,2,3-triazolo[4,5b]pyridinium 3-oxid hexafluorophosphate
$IC_{50}$: half inhibition concentration
IPA: isopropanol
LCMS liquid chromatography-mass spectrometry
L-DATA: Di-p-anisoyl-L-tartaric acid
MS: mass spectrometry
prep-HPLC: preparative high performance liquid chromatography
rt: room temperature
RuPhos Pd G2: chloro(2-dicyclohexylphosphino-2',6'-diisopropoxy-1,1'-biphenyl)[2-(2'-amino-1,1'-biphenyl)] palladium(II) 2nd generation
SFC: supercritical fluid chromatography
TEA: triethylamine
TEMPO: tetramethylpiperidinooxy
TFA: trifluoroacetic acid
THF: tetrahydrofuran
v/v: volume ratio
DDI: drug-drug-interaction
LYSA: lyophilisation solubility assay
HLM: human liver microsome General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel brand and pore size: i) KP-SIL 60 Å, particle size: 40-60 µm; ii) CAS registry NO: Silica Gel: 63231-67-4, particle size:

47-60 micron silica gel; iii) ZCX from Qingdao Haiyang Chemical Co., Ltd, pore: 200-300 or 300-400.

Intermediates and final compounds were purified by preparative HPLC on reversed phase column using XBridge™ Prep-C18 (5 μm, OBDTM 30×100 mm) column, SunFire™ Prep-C18 (5 μm, OBD™ 30×100 mm) column, Phenomenex Synergi-C18 (10 μm, 25×150 mm) or Phenomenex Gemini-C18 (10 μm, 25×150 mm). Waters AutoP purification System (Sample Manager 2767, Pump 2525, Detector: Micromass ZQ and UV 2487, solvent system: acetonitrile and 0.1% ammonium hydroxide in water; acetonitrile and 0.1% FA in water or acetonitrile and 0.1% TFA in water). Or Gilson-281 purification System (Pump 322, Detector: UV 156, solvent system: acetonitrile and 0.05% ammonium hydroxide in water; acetonitrile and 0.225% FA in water; acetonitrile and 0.05% HCl in water; acetonitrile and 0.075% TFA in water; or acetonitrile and water).

For SFC chiral separation, intermediates were separated by chiral column (Daicel chiralpak IC, 5 μm, 30×250 mm), AS (10 μm, 30×250 mm) or AD (10 μm, 30×250 mm) using Mettler Toledo Multigram III system SFC, Waters 80Q preparative SFC or Thar 80 preparative SFC, solvent system: $CO_2$ and IPA (0.5% TEA in IPA) or $CO_2$ and MeOH (0.1% $NH_3 \cdot H_2O$ in MeOH), back pressure 100 bar, detection UV@ 254 or 220 nm.

LC/MS spectra of compounds were obtained using a LC/MS (Waters™ Alliance 2795-Micromass ZQ, Shimadzu Alliance 2020-Micromass ZQ or Agilent Alliance 6110-Micromass ZQ), LC/MS conditions were as follows (running time 3 or 1.5 mins):

Acidic condition I: A: 0.1% TFA in $H_2O$; B: 0.1% TFA in acetonitrile;

Acidic condition II: A: 0.0375% TFA in $H_2O$; B: 0.01875% TFA in acetonitrile;

Basic condition I: A: 0.1% $NH_3 \cdot H_2O$ in $H_2O$; B: acetonitrile;

Basic condition II: A: 0.025% $NH_3 \cdot H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion $(MH)^+$.

NMR Spectra were obtained using Bruker Avance 400 MHz.

The microwave assisted reactions were carried out in a Biotage Initiator Sixty microwave synthesizer. All reactions involving air-sensitive reagents were performed under an argon or nitrogen atmosphere. Reagents were used as received from commercial suppliers without further purification unless otherwise noted.

PREPARATIVE EXAMPLES

The following examples are intended to illustrate the meaning of the present invention but should by no means represent a limitation within the meaning of the present invention:

Example 1

(2R,6R)-4-(7-cyanopyrazolo[1,5-a]pyridin-4-yl)-6-methyl-N-(1-methyl-4-piperidyl)morpholine-2-carboxamide

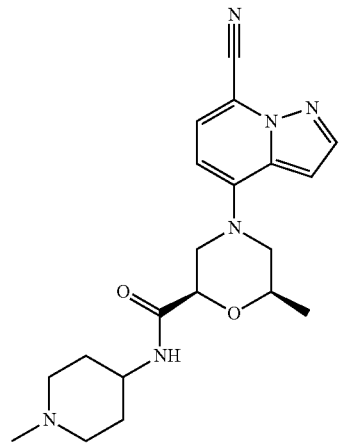 [SMILES: C[C@@H]1CN(c2ccc(C#N)n3nccc23)C[C@H](C(=O)NC2CCN(C)CC2)O1]

The title compound was prepared according to the following scheme:

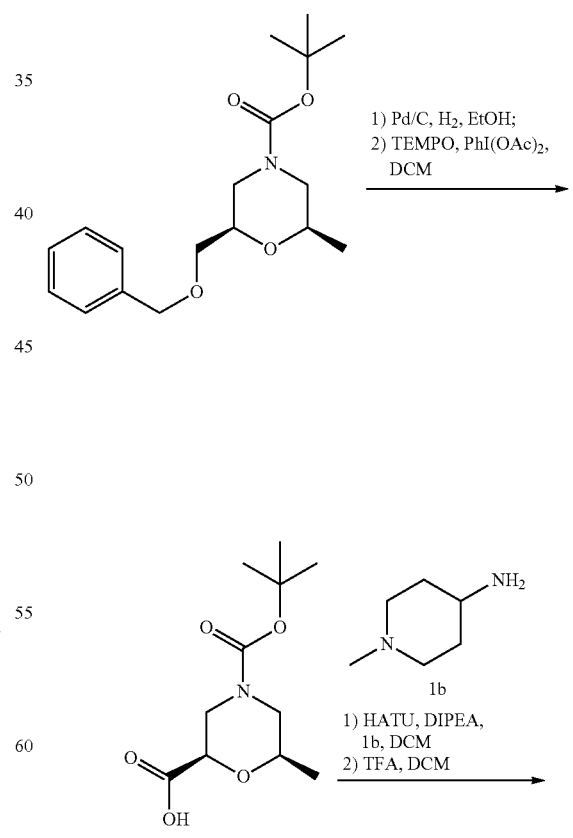

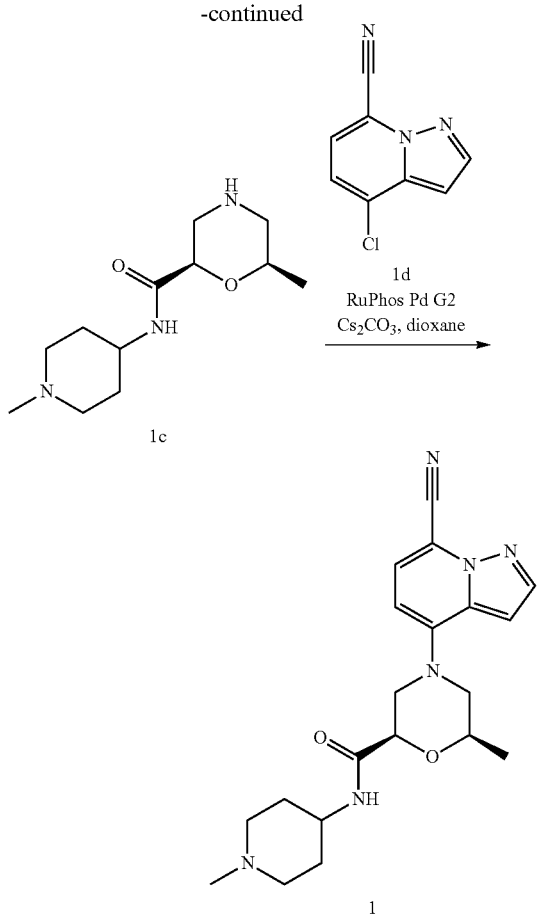

Step 1: preparation of (2R,6R)-4-tert-butoxycarbonyl-6-methyl-morpholine-2-carboxylic Acid (Compound 1a)

To a solution of tert-butyl (2R,6R)-2-(benzyloxymethyl)-6-methyl-morpholine-4-carboxylate (Reference: US 20150105370 A1) (22.0 g, 68.4 mmol) in EtOH (500 mL) was added Pd/C (7.28 g, 10% wet) and stirred for 48 h at 30° C. under H$_2$ atmosphere. The solution was filtered, and the filtrate was concentrated to give intermediate (15 g) as a colorless oil which was dissolved in DCM/H$_2$O (450 mL, v/v=4:1). To the solution was added iodobenzene diacetate (41.8 g, 130 mmol) and TEMPO (2.03 g, 13.0 mmol) at 0° C. The mixture was stirred at 0° C. for additional 0.5 h, then DCM was removed under reduced pressure and H$_2$O (500 mL) was added. The mixture was quenched by adding sat. Na$_2$CO$_3$ to pH around 9 at 0° C., then extracted with EtOAc. The aqueous phase was acidified with citric acid to pH around 3 at 0° C., and extracted with EtOAc. The organic layer was washed with water and brine, dried over Na$_2$SO$_4$, and concentrated to give compound 1a (10 g) as a white solid. $^1$H NMR (400 MHz, METHANOL-d$_4$) δ=4.24 (d, J=12.2 Hz, 1H), 4.11 (dd, J=3.0, 11.0 Hz, 1H), 3.92 (d, J=13.4 Hz, 1H), 3.67-3.56 (m, 1H), 2.91-2.68 (m, 1H), 2.55 (m, 1H), 1.50 (s, 9H), 1.24 (d, J=6.2 Hz, 3H).

Step 2: preparation of (2R,6R)-6-methyl-N-(1-methyl-4-piperidyl)morpholine-2-carboxamide (Compound 1c)

To a solution of (2R,6R)-4-tert-butoxycarbonyl-6-methyl-morpholine-2-carboxylic acid (compound 1a, 100 mg, 0.41 mmol), 1-methylpiperidin-4-amine (compound 1b, 56 mg, 61 µl, 0.49 mmol) and DIPEA (105 mg, 142 µl, 0.82 mmol) in DCM (3 mL) was added HATU (233 mg, 0.61 mmol) at 0° C. The mixture was stirred at rt overnight, then diluted with DCM (20 mL), washed with sat. NH$_4$Cl, the aqueous layer was extracted with DCM (20 mL), and the combined organic layer was washed with brine, dried over Na$_2$SO$_4$, and concentrated to give a pale yellow oil, which was dissolved in DCM (2 mL). The solution was then cooled with ice water, TFA (1 mL) was added. The mixture was warmed to rt and stirred for 2 hrs, then concentrated to give a crude compound 1c (169 mg) which was directly used in next step. MS: calc'd 242 (MH$^+$), measured 242 (MH$^+$).

Step 3: Preparation of (2R,6R)-4-(7-cyanopyrazolo[1,5-a]pyridin-4-yl)-6-methyl-N-(1-methyl-4-piperidyl)morpholine-2-carboxamide (Example 1)

To a solution of 4-chloropyrazolo[1,5-a]pyridine-7-carbonitrile (CAS: 1268520-74-6, Pharmablock) (compound 1d, 25 mg, 0.14 mmol), (2R,6R)-6-methyl-N-(1-methyl-4-piperidyl)morpholine-2-carboxamide 2,2,2-trifluoroacetate (compound 1c, 65 mg, 0.18 mmol), and Cs$_2$CO$_3$ (183 mg, 0.56 mmol) in 1,4-dioxane (3 mL) was added Ruphos Pd G2 (11 mg, 14 µmol). The reaction mixture was heated at 90° C. (oil bath) under N$_2$ for 2 h, then cooled to rt, diluted with EtOAc and filtered through celite, the filtrate was concentrated to give a brown oil which was purified by prep-HPLC to give Example 1 (20 mg) as a white powder. MS: calc'd 383 (MH$^+$), measured 383 (MH$^+$). $^1$H NMR (400 MHz, METHANOL-d$_4$) δ 8.04 (d, J=2.3 Hz, 1H), 7.46 (d, J=8.1 Hz, 1H), 6.90 (d, J=2.3 Hz, 1H), 6.61 (d, J=8.1 Hz, 1H), 4.32 (dd, J=2.6, 10.8 Hz, 1H), 4.08 (br d, J=12.5 Hz, 1H), 4.04-3.94 (m, 1H), 3.84-3.67 (m, 2H), 2.88 (br d, J=10.6 Hz, 2H), 2.85-2.66 (m, 2H), 2.29 (s, 3H), 2.15 (br t, J=11.6 Hz, 2H), 1.94-1.77 (m, 2H), 1.75-1.49 (m, 2H), 1.35 (d, J=6.1 Hz, 3H).

Example 2

(2R,6R)-4-(7-cyanopyrazolo[1,5-a]pyridin-4-yl)-N-[(3S,4R)-4-fluoropyrrolidin-3-yl]-6-methyl-morpholine-2-carboxamide

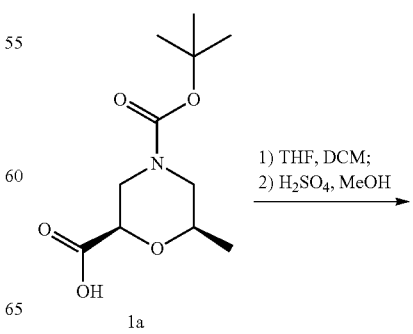

-continued

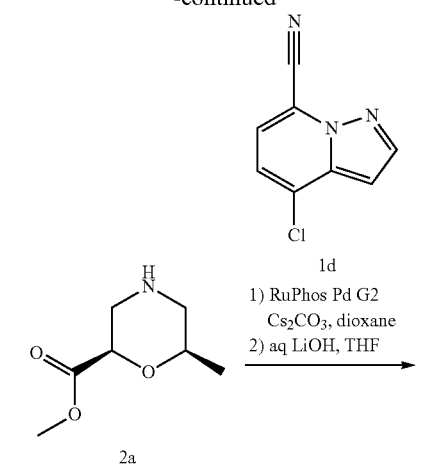

1) RuPhos Pd G2
   Cs₂CO₃, dioxane
2) aq LiOH, THF

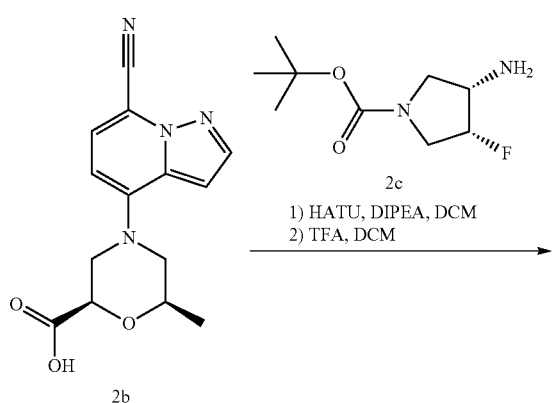

1) HATU, DIPEA, DCM
2) TFA, DCM

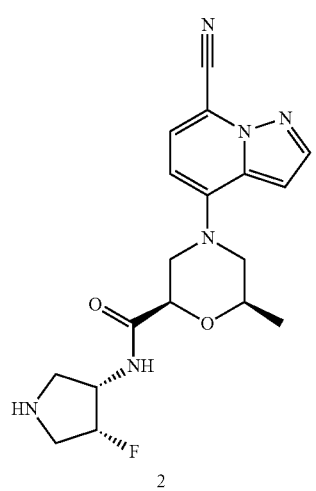

The title compound was prepared according to the following scheme:

Step 1: Preparation of methyl (2R,6R)-6-methylmorpholine-2-carboxylate (Compound 2a)

To a suspension of (2R,6R)-4-tert-butoxycarbonyl-6-methyl-morpholine-2-carboxylic acid (compound 1a, 125 mg, 0.51 mmol) in DCM (2 mL) was added TFA (0.5 mL). The reaction mixture was stirred at rt for 2 hrs, then concentrated to give a pale yellow oil. The oil was dissolved in MeOH (3 mL). To the solution was added one drop of $H_2SO_4$. The mixture was heated at 60° C. (oil bath) overnight, then diluted with MeOH. To the solution was added solid $Na_2CO_3$, the suspension was stirred at rt for 30 min, then filtered through celite, and the filtrate was concentrated to give a pale yellow oil (133 mg) which was directly used in next step. MS: calc'd 160 (MH⁺), measured 160 (MH⁺).

Step 2: preparation of (2R,6R)-4-(7-cyanopyrazolo[1,5-a]pyridin-4-yl)-6-methyl-morpholine-2-carboxylic Acid (Compound 2b)

To a solution of 4-chloropyrazolo[1,5-a]pyridine-7-carbonitrile (compound 1d, 40 mg, 0.22 mmol), methyl (2R,6R)-6-methylmorpholine-2-carboxylate (compound 2a, 65 mg, 0.18 mmol), $Cs_2CO_3$ (294 mg, 0.90 mmol) in 1,4-dioxane (5 mL) was added Ruphos Pd G2 (17 mg, 22 μmol). The reaction mixture was heated at 90° C. (oil bath) under $N_2$ for 3 hrs, then cooled to rt and diluted with EtOAc and filtered through celite, the filtrate was concentrated to give a brown oil. The oil was dissolved in THF (2 mL). To the solution was added aq. LiOH (2 M in water, 1 mL, 2.0 mmol). The mixture was stirred at rt for 1 hrs, then pH was adjusted to 1~2 with aq. HCl, then extracted with DCM. The organic layer was washed with brine, dried over $Na_2SO_4$, and concentrated to give a crude compound 2b (80 mg) which was directly used in next step. MS: calc'd 287 (MH⁺), measured 287 (MH⁺).

Step 3: preparation of (2R,6R)-4-(7-cyanopyrazolo[1,5-a]pyridin-4-yl)-N-[(3S,4R)-4-fluoropyrrolidin-3-yl]-6-methyl-morpholine-2-carboxamide (Example 2)

To a solution of (2R,6R)-4-(7-cyanopyrazolo[1,5-a]pyridin-4-yl)-6-methyl-morpholine-2-carboxylic acid (compound 2b, 50 mg, 0.17 mmol), (3S,4R)-tert-butyl 3-amino-4-fluoropyrrolidine-1-carboxylate (CAS: 1174020-30-4, Pharmablock) (compound 2c, 54 mg, 0.26 mmol) and DPIEA (135 mg, 178 μL, 1.05 mmol) in DCM (3 mL) was added HATU (133 mg, 0.35 mmol). The mixture was stirred at rt overnight, then diluted with DCM, washed with sat. $NH_4Cl$ and brine, dried over $Na_2SO_4$, and concentrated to give a pale yellow oil. The oil was dissolved in DCM (2 mL), and cooled with ice water. To the solution was added TFA (0.5 mL). The mixture was warmed to rt, and stirred at rt for 1 h, then concentrated to give a crude product which was purified by prep-HPLC to give Example 2 (19 mg) as a white powder. MS: calc'd 373 (MH$^+$), measured 373 (MH$^+$). $^1$H NMR (400 MHz, METHANOL-d$_4$) δ 7.95 (d, J=2.3 Hz, 1H), 7.39 (d, J=7.9 Hz, 1H), 6.81 (d, J=2.4 Hz, 1H), 6.54 (d, J=7.9 Hz, 1H), 5.32-5.13 (m, 1H), 4.72-4.56 (m, 1H), 4.35 (dd, J=2.8, 10.8 Hz, 1H), 4.01 (td, J=2.2, 12.4 Hz, 1H), 3.98-3.89 (m, 1H), 3.69-3.56 (m, 3H), 3.53-3.46 (m, 1H), 3.32 (t, J=11.2 Hz, 1H), 2.75 (dd, J=10.9, 12.4 Hz, 1H), 2.63 (dd, J=10.4, 12.5 Hz, 1H), 1.26 (d, J=6.4 Hz, 3H).

Example 3

(2R,6R)-N-(2-azaspiro[3.3]heptan-6-yl)-4-(7-cyano-pyrazolo[1,5-a]pyridin-4-yl)-6-methyl-morpholine-2-carboxamide The title compound was prepared in analogy to the preparation of Example 2 by using tert-butyl 6-amino-2-azaspiro[3.3]heptane-2-carboxylate instead of (3S,4R)-tert-butyl 3-amino-4-fluoropyrrolidine-1-carboxylate (compound 2c). Example 3 (11 mg) was obtained as a grey solid. MS: calc'd 381 (MH$^+$), measured 381 (MH$^+$). $^1$H NMR (400 MHz, METHANOL-d$_4$) δ 8.04 (d, J=2.4 Hz, 1H), 7.47 (d, J=8.1 Hz, 1H), 6.89 (d, J=2.4 Hz, 1H), 6.62 (d, J=7.9 Hz, 1H), 4.34-4.20 (m, 2H), 4.17-4.12 (m, 2H), 4.11-4.02 (m, 3H), 4.02-3.94 (m, 1H), 3.74 (td, J=2.1, 12.4 Hz, 1H), 2.81-2.72 (m, 1H), 2.72-2.62 (m, 3H), 2.44-2.34 (m, 2H), 1.35 (d, J=6.2 Hz, 3H).

Example 4

(2R,6R)-4-(7-cyanopyrazolo[1,5-a]pyridin-4-yl)-6-methyl-N-tetrahydropyran-4-yl-morpholine-2-carboxamide

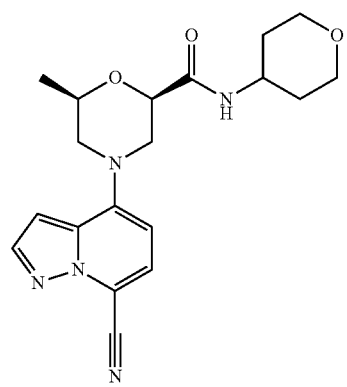 [SMILES: C[C@@H]1CN(c2ccc(C#N)n3nccc23)C[C@H](C(=O)NC2CCOCC2)O1]

The title compound was prepared according to the following scheme:

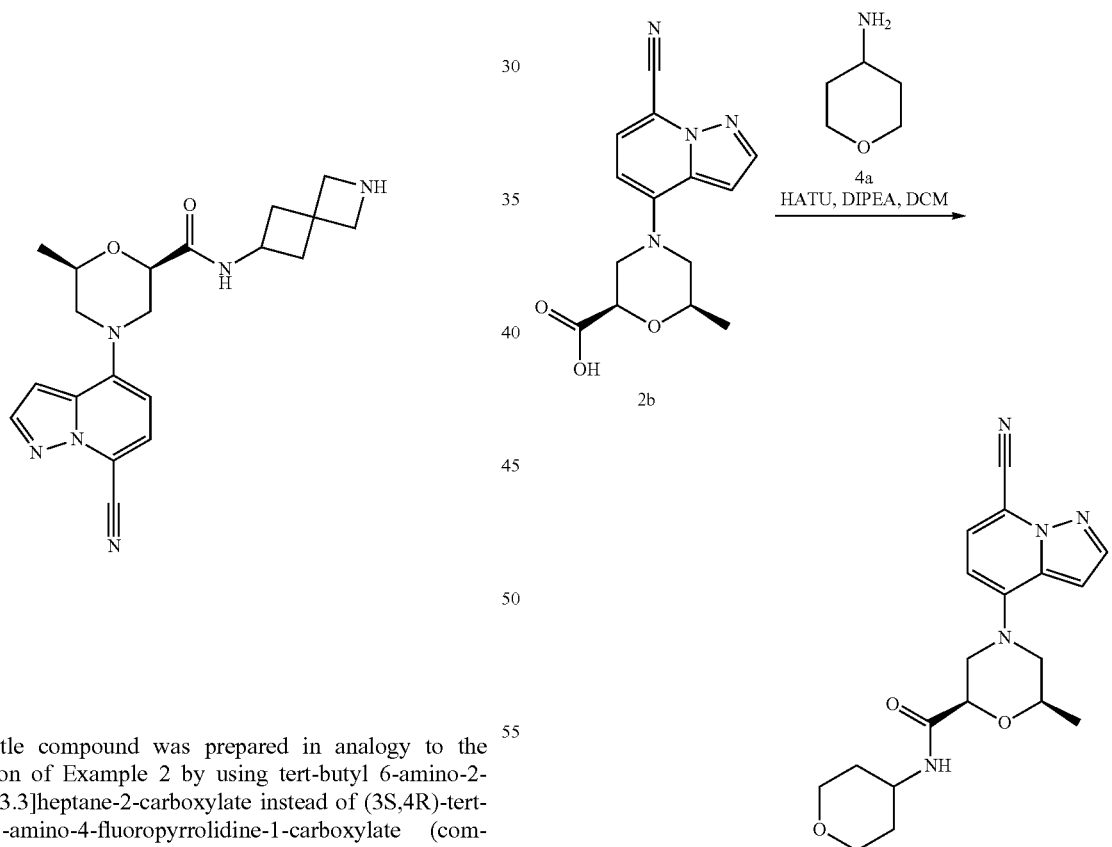

To a solution of (2R,6R)-4-(7-cyanopyrazolo[1,5-a]pyridin-4-yl)-6-methyl-morpholine-2-carboxylic acid (compound 2b, 30 mg, 0.11 mmol), tetrahydropyran-4-amine (compound 4a, 13 mg, 0.13 mmol) and DIPEA (54 mg, 73 μL, 0.42 mmol) in DCM (3 mL) was added HATU (60 mg, 0.16 mmol). The reaction mixture was stirred at rt overnight, then diluted with DCM, washed with sat. NH₄Cl and brine, dried over Na₂SO₄, and concentrated to give a crude product which was purified by prep-HPLC to give Example 4 (13 mg) as a grey solid. MS: calc'd 370 (MH⁺), measured 370 (MH⁺). ¹H NMR (400 MHz, METHANOL-d₄) δ 8.05 (d, J=2.3 Hz, 1H), 7.48 (d, J=7.9 Hz, 1H), 6.92 (d, J=2.4 Hz, 1H), 6.63 (d, J=7.9 Hz, 1H), 4.33 (dd, J=2.8, 10.8 Hz, 1H), 4.12-4.06 (m, 1H), 4.04-3.91 (m, 4H), 3.75 (br d, J=12.5 Hz, 1H), 3.52-3.45 (m, 2H), 2.85-2.69 (m, 2H), 1.80 (ddd, J=2.2, 10.8, 12.8 Hz, 2H), 1.70-1.59 (m, 2H), 1.35 (d, J=6.2 Hz, 3H).

Example 5

Cis-(2R,6R)-4-(7-cyanopyrazolo[1,5-a]pyridin-4-yl)-6-methyl-N-(4-fluoropyrrolidin-3-yl) morpholine-2-carboxamide (Mixture of Two Cis Diastereoisomers at the Position Marked with *)

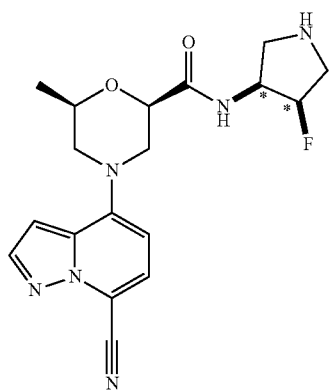

The title compound was prepared in analogy to the preparation of Example 2 by using cis-tert-butyl 3-amino-4-fluoropyrrolidine-1-carboxylate (CAS: 1431720-86-3, Pharmablock) instead of (3S,4R)-tert-butyl 3-amino-4-fluoropyrrolidine-1-carboxylate (compound 2c). Example 5 (11 mg) was obtained as a grey solid. MS: calc'd 373 (MH⁺), measured 373 (MH⁺). ¹H NMR (400 MHz, METHANOL-d₄) δ 8.05 (d, J=2.4 Hz, 1H), 7.48 (d, J=8.1 Hz, 1H), 6.90 (dd, J=1.4, 2.4 Hz, 1H), 6.64 (dd, J=1.7, 8.0 Hz, 1H), 5.43-5.21 (m, 1H), 4.82-4.66 (m, 1H), 4.44 (ddd, J=2.7, 6.2, 10.8 Hz, 1H), 4.11 (qd, J=2.3, 12.4 Hz, 1H), 4.07-3.98 (m, 1H), 3.79-3.57 (m, 4H), 3.42 (dt, J=4.6, 11.2 Hz, 1H), 2.85 (ddd, J=3.7, 10.9, 12.4 Hz, 1H), 2.74 (ddd, J=3.8, 10.4, 12.5 Hz, 1H), 1.36 (d, J=5.9 Hz, 3H).

Example 6

(2R,6R)-N-(azepan-4-yl)-4-(7-cyanopyrazolo[1,5-a]pyridin-4-yl)-6-methyl-morpholine-2-carboxamide

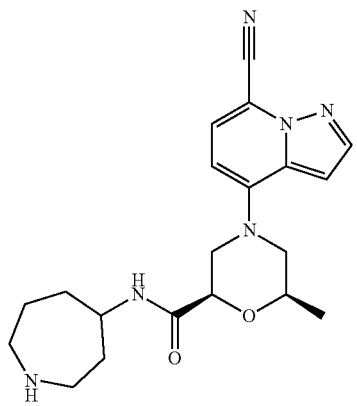 [SMILES: C[C@@H]1CN(c2ccc(C#N)n3nccc23)C[C@H](C(=O)NC2CCCNCC2)O1]

The title compound was prepared in analogy to the preparation of Example 2 by using tert-butyl 4-amino-azepane-1-carboxylate instead of (3S,4R)-tert-butyl 3-amino-4-fluoropyrrolidine-1-carboxylate (compound 2c). Example 6 (11 mg) was obtained as a grey solid. MS: calc'd 383 (MH⁺), measured 383 (MH⁺). ¹H NMR (400 MHz, METHANOL-d₄) δ 8.04 (d, J=2.4 Hz, 1H), 7.47 (d, J=7.9 Hz, 1H), 6.90 (d, J=2.1 Hz, 1H), 6.62 (d, J=8.1 Hz, 1H), 4.34 (dd, J=2.6, 10.8 Hz, 1H), 4.09 (td, J=2.2, 12.5 Hz, 1H), 4.06-3.96 (m, 2H), 3.74 (br d, J=12.3 Hz, 1H), 3.41-3.33 (m, 2H), 3.26-3.14 (m, 2H), 2.85-2.76 (m, 1H), 2.72 (t, J=11.4 Hz, 1H), 2.22-1.92 (m, 4H), 1.91-1.68 (m, 2H), 1.35 (d, J=6.2 Hz, 3H).

Example 7

(2R,6R)-4-(7-cyanopyrazolo[1,5-a]pyridin-4-yl)-6-methyl-N-[(4-methylmorpholin-2-yl)methyl]morpholine-2-carboxamide

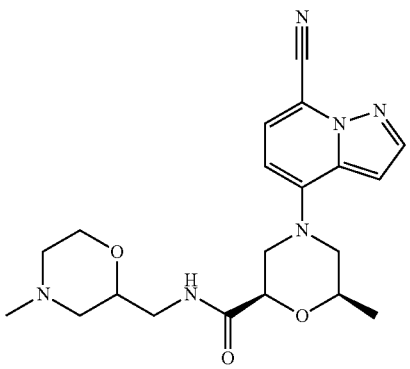 [SMILES: C[C@@H]1CN(c2ccc(C#N)n3nccc23)C[C@H](C(=O)NCC2CN(C)CCO2)O1]

The title compound was prepared in analogy to the preparation of Example 4 by using (4-methylmorpholin-2-yl)methanamine instead of tetrahydropyran-4-amine (compound 4a). Example 7 (11 mg) was obtained as a grey solid. MS: calc'd 399 (MH⁺), measured 399 (MH⁺). ¹H NMR (400 MHz, METHANOL-d₄) δ 8.04 (d, J=2.4 Hz, 1H), 7.47 (d, J=7.9 Hz, 1H), 6.90 (d, J=2.3 Hz, 1H), 6.62 (d, J=7.9 Hz, 1H), 4.38 (td, J=2.3, 10.6 Hz, 1H), 4.20-4.07 (m, 2H), 4.06-3.96 (m, 1H), 3.89-3.70 (m, 3H), 3.55-3.36 (m, 4H), 3.17-3.06 (m, 1H), 2.93 (s, 3H), 2.90-2.77 (m, 2H), 2.77-2.67 (m, 1H), 1.35 (d, J=6.2 Hz, 3H).

Example 8

4-[(2R,6R)-2-(3-aminoazetidine-1-carbonyl)-6-methyl-morpholin-4-yl]pyrazolo[1,5a]pyridine-7-carbonitrile

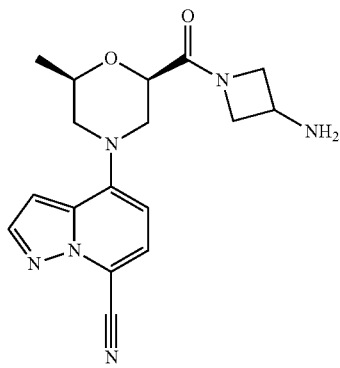 [SMILES: C[C@@H]1CN(c2ccc(C#N)n3nccc23)C[C@H](C(=O)N2CC(N)C2)O1]

The title compound was prepared in analogy to the preparation of Example 2 by using tert-butyl N-(azetidin-3-yl)carbamate instead of (3S,4R)-tert-butyl 3-amino-4-fluoropyrrolidine-1-carboxylate (compound 2c). Example 8 (10 mg) was obtained as a grey solid. MS: calc'd 341 (MH+), measured 341 (MH+). $^1$H NMR (400 MHz, METHANOL-d$_4$) δ 8.06 (d, J=2.3 Hz, 1H), 7.51 (d, J=7.9 Hz, 1H), 6.90 (d, J=1.2 Hz, 1H), 6.65 (d, J=7.9 Hz, 1H), 4.86-4.73 (m, 1H), 4.57-4.47 (m, 1H), 4.44-4.29 (m, 2H), 4.12-3.88 (m, 4H), 3.81-3.73 (m, 1H), 2.95 (ddd, J=8.0, 10.9, 12.4 Hz, 1H), 2.71 (ddd, J=6.5, 10.5, 12.4 Hz, 1H), 1.33 (d, J=6.2 Hz, 3H).

Example 9

(2R,6R)-4-(7-cyanopyrazolo[1,5-a]pyridin-4-yl)-N-(2-methoxyethyl)-6-methyl-morpholine-2-carboxamide

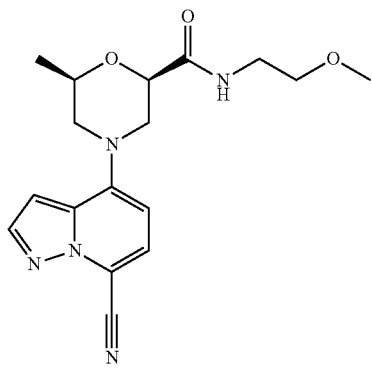 [SMILES: COCCNC(=O)[C@H]1CN(c2ccc(C#N)n3nccc23)C[C@@H](C)O1]

The title compound was prepared in analogy to the preparation of Example 4 by using 2-methoxyethanamine instead of tetrahydropyran-4-amine (compound 4a). Example 9 (9 mg) was obtained as a white powder. MS: calc'd 344 (MH+), measured 344 (MH+). $^1$H NMR (400 MHz, METHANOL-d$_4$) δ 8.05 (d, J=2.4 Hz, 1H), 7.48 (d, J=7.9 Hz, 1H), 6.92 (d, J=2.4 Hz, 1H), 6.63 (d, J=7.9 Hz, 1H), 4.35 (dd, J=2.8, 10.8 Hz, 1H), 4.11 (td, J=2.3, 12.5 Hz, 1H), 4.06-3.96 (m, 1H), 3.75 (td, J=2.1, 12.4 Hz, 1H), 3.51-3.41 (m, 4H), 3.36 (s, 3H), 2.85-2.68 (m, 2H), 1.35 (d, J=6.2 Hz, 3H).

Example 10

(2R,6R)-4-(7-cyanopyrazolo[1,5-a]pyridin-4-yl)-N-[2-(2-hydroxyethoxy)ethyl]-6-methyl-morpholine-2-carboxamide

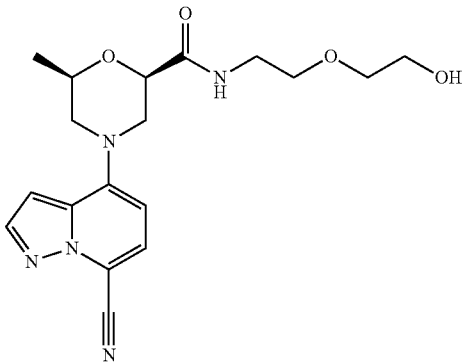 [SMILES: C[C@@H]1CN(c2ccc(C#N)n3nccc23)C[C@H](C(=O)NCCOCCO)O1]

The title compound was prepared in analogy to the preparation of Example 4 by using 2-(2-aminoethoxy)ethanol instead of tetrahydropyran-4-amine (compound 4a). Example 10 (6 mg) was obtained as a white powder. MS: calc'd 374 (MH+), measured 374 (MH+). $^1$H NMR (400 MHz, METHANOL-d$_4$) δ 7.95 (d, J=2.4 Hz, 1H), 7.38 (d, J=7.9 Hz, 1H), 6.82 (d, J=2.4 Hz, 1H), 6.53 (d, J=8.1 Hz, 1H), 4.25 (dd, J=2.7, 10.9 Hz, 1H), 4.01 (td, J=2.3, 12.5 Hz, 1H), 3.96-3.86 (m, 1H), 3.65 (td, J=2.1, 12.4 Hz, 1H), 3.60-3.54 (m, 2H), 3.51-3.43 (m, 4H), 3.40-3.33 (m, 2H), 2.71 (dd, J=10.9, 12.3 Hz, 1H), 2.62 (dd, J=10.5, 12.5 Hz, 1H), 1.25 (d, J=6.2 Hz, 3H).

Example 11

(2R,6R)-N-(1-cyanocyclopropyl)-4-(7-cyanopyrazolo[1,5-a]pyridin-4-yl)-6-methyl-morpholine-2-carboxamide

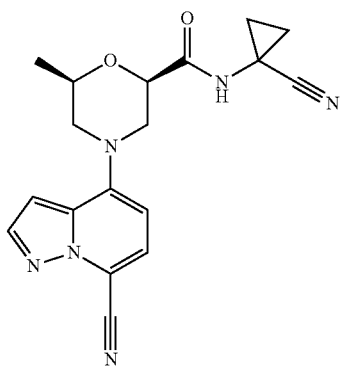 [SMILES: C[C@@H]1CN(c2ccc(C#N)n3nccc23)C[C@H](C(=O)NC2(C#N)CC2)O1]

The title compound was prepared in analogy to the preparation of Example 4 by using 1-aminocyclopropanecarbonitrile instead of tetrahydropyran-4-amine (compound 4a). Example 11 (9 mg) was obtained as a white powder. MS: calc'd 351 (MH$^+$), measured 351 (MH$^+$). $^1$H NMR (400 MHz, METHANOL-d$_4$) δ 8.05 (d, J=2.3 Hz, 1H), 7.48 (d, J=7.9 Hz, 1H), 6.90 (d, J=2.4 Hz, 1H), 6.64 (d, J=8.1 Hz, 1H), 4.37 (dd, J=2.8, 10.9 Hz, 1H), 4.07 (td, J=2.4, 12.5 Hz, 1H), 4.04-3.94 (m, 1H), 3.75 (td, J=2.1, 12.5 Hz, 1H), 2.83 (dd, J=10.9, 12.5 Hz, 1H), 2.70 (dd, J=10.5, 12.5 Hz, 1H), 1.56-1.50 (m, 2H), 1.34 (d, J=6.2 Hz, 3H), 1.32-1.25 (m, 2H).

Example 12

(2R,6R)-N-(1-adamantyl)-4-(7-cyanopyrazolo[1,5-a]pyridin-4-yl)-6-methyl-morpholine-2-carboxamide

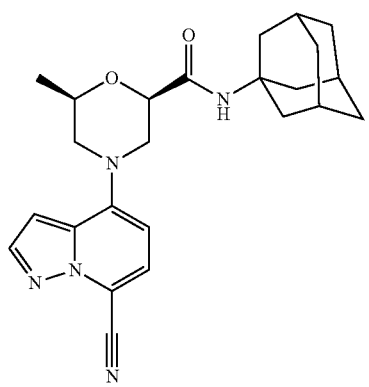 [SMILES: C[C@@H]1CN(c2ccc(C#N)n3nccc23)C[C@H](C(=O)NC23CC4CC(CC(C4)C2)C3)O1]

The title compound was prepared in analogy to the preparation of Example 4 by using adamantan-1-amine instead of tetrahydropyran-4-amine (compound 4a). Example 12 (12 mg) was obtained as a white powder. MS: calc'd 420 (MH$^+$), measured 420 (MH$^+$). $^1$H NMR (400 MHz, METHANOL-d$_4$) δ 8.04 (d, J=2.3 Hz, 1H), 7.47 (d, J=7.9 Hz, 1H), 6.90 (d, J=2.4 Hz, 1H), 6.62 (d, J=7.9 Hz, 1H), 4.21 (dd, J=2.7, 10.9 Hz, 1H), 4.06 (td, J=2.3, 12.5 Hz, 1H), 4.03-3.93 (m, 1H), 3.73 (td, J=2.1, 12.5 Hz, 1H), 2.83-2.66 (m, 2H), 2.08 (br s, 3H), 2.06 (s, 6H), 1.74 (br s, 6H), 1.33 (d, J=6.2 Hz, 3H).

Example 13

(2R,6R)-4-(7-cyanopyrazolo[1,5-a]pyridin-4-yl)-N-(2-hydroxybutyl)-6-methyl-morpholine-2-carboxamide

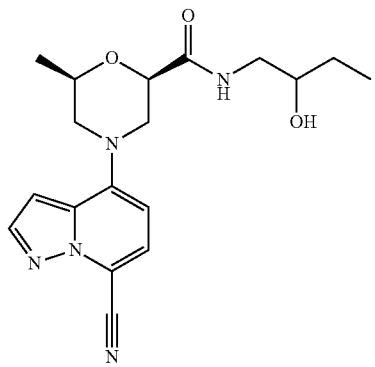 [SMILES: CCC(O)CNC(=O)[C@H]1CN(c2ccc(C#N)n3nccc23)C[C@@H](C)O1]

The title compound was prepared in analogy to the preparation of Example 4 by using 1-aminobutan-2-ol instead of tetrahydropyran-4-amine (compound 4a). Example 13 (4 mg) was obtained as a white powder. MS: calc'd 358 (MH$^+$), measured 358 (MH$^+$). $^1$H NMR (400 MHz, METHANOL-d$_4$) δ 8.05 (d, J=2.3 Hz, 1H), 7.48 (d, J=8.1 Hz, 1H), 6.92 (d, J=2.1 Hz, 1H), 6.64 (d, J=8.1 Hz, 1H), 4.36 (td, J=2.3, 10.5 Hz, 1H), 4.12 (br d, J=12.5 Hz, 1H), 4.06-3.97 (m, 1H), 3.78-3.72 (m, 1H), 3.63-3.54 (m, 1H), 3.44-3.36 (m, 1H), 3.21-3.12 (m, 1H), 2.86-2.78 (m, 1H), 2.73 (t, J=11.1 Hz, 1H), 1.58-1.38 (m, 2H), 1.35 (d, J=6.2 Hz, 3H), 0.97 (t, J=7.5 Hz, 3H).

Example 14

(2R,6R)-N-(9-azabicyclo[3.3.1]nonan-3-yl)-4-(7-cyanopyrazolo[1,5-a]pyridin-4-yl)-6-methyl-morpholine-2-carboxamide

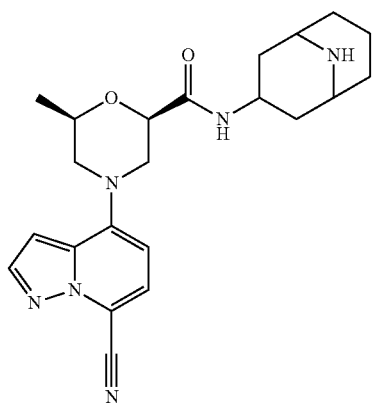 [SMILES: C[C@@H]1CN(c2ccc(C#N)n3nccc23)C[C@H](C(=O)NC2CC3CCCC(C2)N3)O1]

The title compound was prepared in analogy to the preparation of Example 2 by using tert-butyl 3-amino-9-azabicyclo[3.3.1]nonane-9-carboxylate (CAS: 202797-03-3, Pharmablock) instead of (3S,4R)-tert-butyl 3-amino-4-fluoropyrrolidine-1-carboxylate (compound 2c). Example 14 (32 mg) was obtained as a white powder. MS: calc'd 409 (MH+), measured 409 (MH+). $^1$H NMR (400 MHz, METHANOL-d$_4$) δ 8.05 (d, J=2.3 Hz, 1H), 7.48 (d, J=7.9 Hz, 1H), 6.91 (d, J=2.4 Hz, 1H), 6.63 (d, J=7.9 Hz, 1H), 4.84-4.72 (m, 1H), 4.36 (dd, J=2.7, 10.8 Hz, 1H), 4.14-4.07 (m, 1H), 4.06-3.95 (m, 1H), 3.75 (br dd, J=2.2, 9.9 Hz, 3H), 2.81 (dd, J=10.9, 12.5 Hz, 1H), 2.72 (dd, J=10.5, 12.5 Hz, 1H), 2.29-2.17 (m, 2H), 2.15-1.94 (m, 7H), 1.86-1.77 (m, 1H), 1.35 (d, J=6.2 Hz, 3H).

Example 15

(2R,6R)-4-(7-cyanopyrazolo[1,5-a]pyridin-4-yl)-N-[3-(hydroxymethyl)-1-bicyclo[1.1.1]pentanyl]-6-methyl-morpholine-2-carboxamide

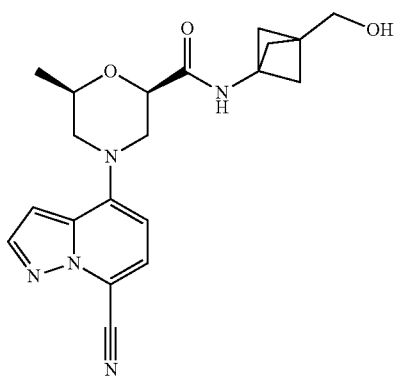 [SMILES: C[C@@H]1CN(c2ccc(C#N)n3nccc23)C[C@H](C(=O)NC23CC(CO)(C2)C3)O1]

The title compound was prepared in analogy to the preparation of Example 4 by using (3-amino-1-bicyclo[1.1.1]pentanyl)methanol instead of tetrahydropyran-4-amine (compound 4a). Example 15 (17 mg) was obtained as a white powder. MS: calc'd 382 (MH+), measured 382 (MH+). $^1$H NMR (400 MHz, METHANOL-d$_4$) δ 8.04 (d, J=2.4 Hz, 1H), 7.47 (d, J=8.1 Hz, 1H), 6.90 (d, J=2.4 Hz, 1H), 6.62 (d, J=8.1 Hz, 1H), 4.27 (dd, J=2.8, 10.8 Hz, 1H), 4.06 (td, J=2.2, 12.4 Hz, 1H), 4.03-3.93 (m, 1H), 3.78-3.70 (m, 1H), 3.61 (s, 2H), 2.80 (dd, J=10.9, 12.5 Hz, 1H), 2.70 (dd, J=10.5, 12.4 Hz, 1H), 2.02 (s, 6H), 1.34 (d, J=6.2 Hz, 3H).

Example 16

(2R,6R)-4-(7-cyanopyrazolo[1,5-a]pyridin-4-yl)-N-(2-hydroxy-1,1-dimethyl-ethyl)-6-methyl-morpholine-2-carboxamide

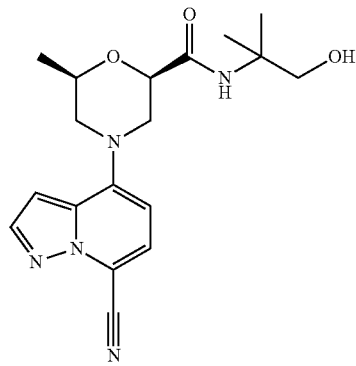 [SMILES: C[C@@H]1CN(c2ccc(C#N)n3nccc23)C[C@H](C(=O)NC(C)(C)CO)O1]

The title compound was prepared in analogy to the preparation of Example 4 by using 2-amino-2-methyl-propan-1-ol instead of tetrahydropyran-4-amine (compound 4a). Example 16 (12 mg) was obtained as a white powder. MS: calc'd 358 (M+), measured 358 (MH+). $^1$H NMR (400 MHz, METHANOL-d$_4$) δ 8.05 (d, J=2.4 Hz, 1H), 7.48 (d, J=7.9 Hz, 1H), 6.91 (d, J=2.4 Hz, 1H), 6.63 (d, J=7.9 Hz, 1H), 4.26 (dd, J=2.7, 10.8 Hz, 1H), 4.09 (td, J=2.3, 12.5 Hz, 1H), 4.05-3.95 (m, 1H), 3.74 (td, J=2.1, 12.5 Hz, 1H), 3.61-3.50 (m, 2H), 2.81 (dd, J=10.9, 12.5 Hz, 1H), 2.72 (dd, J=10.4, 12.5 Hz, 1H), 1.38-1.29 (m, 9H).

Example 17

(2R,6R)-4-(7-cyanopyrazolo[1,5-a]pyridin-4-yl)-N-(1,1-dimethylpropyl)-6-methyl-morpholine-2-carboxamide

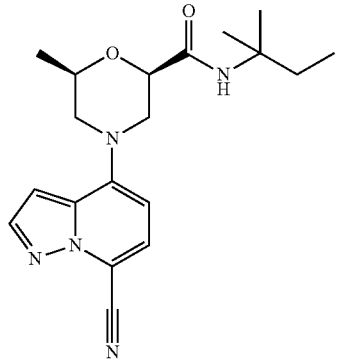 [SMILES: CCC(C)(C)NC(=O)[C@H]1CN(c2ccc(C#N)n3nccc23)C[C@@H](C)O1]

The title compound was prepared in analogy to the preparation of Example 4 by using 2-methylbutan-2-amine instead of tetrahydropyran-4-amine (compound 4a). Example 17 (7 mg) was obtained as a white powder. MS: calc'd 356 (MH−), measured 356 (MH+). $^1$H NMR (400 MHz, METHANOL-d$_4$) δ 8.03 (d, J=2.4 Hz, 1H), 7.46 (d, J=7.9 Hz, 1H), 6.90 (d, J=2.4 Hz, 1H), 6.61 (d, J=8.1 Hz, 1H), 4.24 (dd, J=2.7, 10.9 Hz, 1H), 4.11-4.04 (m, 1H), 4.04-3.95 (m, 1H), 3.77-3.69 (m, 1H), 2.78 (dd, J=10.9, 12.3

Hz, 1H), 2.71 (dd, J=10.4, 12.5 Hz, 1H), 1.84-1.70 (m, 2H), 1.37-1.29 (m, 9H), 0.88 (t, J=7.5 Hz, 3H).

Example 18

(2R,6R)-4-(7-cyanopyrazolo[1,5-a]pyridin-4-yl)-N-[(4,4-difluoropyrrolidin-3-yl)methyl]-6-methyl-morpholine-2-carboxamide

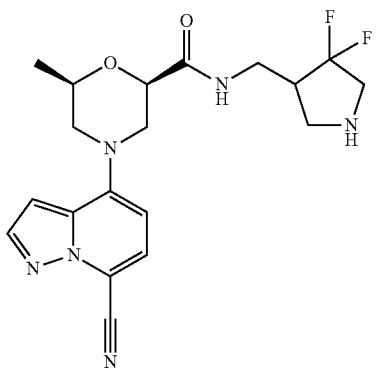 [SMILES: C[C@@H]1CN(c2ccc(C#N)n3nccc23)C[C@H](C(=O)NCC2CNCC2(F)F)O1]

The title compound was prepared in analogy to the preparation of Example 2 by using tert-butyl 4-(aminomethyl)-3,3-difluoro-pyrrolidine-1-carboxylate instead of (3S,4R)-tert-butyl 3-amino-4-fluoropyrrolidine-1-carboxylate (compound 2c). Example 18 (17 mg) was obtained as a white powder. MS: calc'd 405 (MH$^+$), measured 405 (MH$^+$). $^1$H NMR (400 MHz, METHANOL-d$_4$) δ 8.05 (d, J=2.4 Hz, 1H), 7.48 (d, J=8.1 Hz, 1H), 6.91 (d, J=2.4 Hz, 1H), 6.63 (d, J=8.1 Hz, 1H), 4.35 (td, J=2.3, 10.6 Hz, 1H), 4.10 (br d, J=12.1 Hz, 1H), 4.06-3.96 (m, 1H), 3.78-3.71 (m, 1H), 3.51-3.38 (m, 2H), 3.28-3.18 (m, 2H), 3.17-3.04 (m, 1H), 2.84-2.59 (m, 4H), 1.35 (d, J=6.2 Hz, 3H).

Example 19

(2R,6R)-4-(7-cyanopyrazolo[1,5-a]pyridin-4-yl)-6-methyl-N-(4-methyl-4-piperidyl)morpholine-2-carboxamide

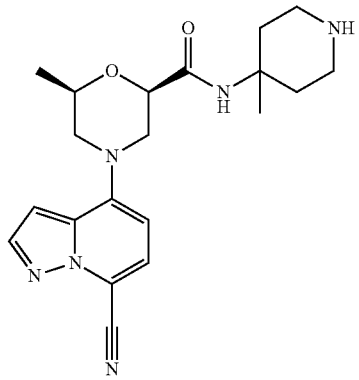 [SMILES: C[C@@H]1CN(c2ccc(C#N)n3nccc23)C[C@H](C(=O)NC2(C)CCNCC2)O1]

The title compound was prepared in analogy to the preparation of Example 2 by using tert-butyl 4-amino-4-methyl-piperidine-1-carboxylate instead of (3S,4R)-tert-butyl 3-amino-4-fluoropyrrolidine-1-carboxylate (compound 2c). Example 19 (23 mg) was obtained as a white powder. MS: calc'd 383 (MH$^+$), measured 383 (MH$^+$). $^1$H NMR (400 MHz, METHANOL-d$_4$) δ 8.05 (d, J=2.3 Hz, 1H), 7.49 (d, J=7.9 Hz, 1H), 6.90 (d, J=2.4 Hz, 1H), 6.64 (d, J=7.9 Hz, 1H), 4.32 (dd, J=2.6, 10.8 Hz, 1H), 4.07 (td, J=2.3, 12.4 Hz, 1H), 4.05-3.97 (m, 1H), 3.80-3.71 (m, 1H), 3.27 (br d, J=12.7 Hz, 2H), 3.19-3.08 (m, 2H), 2.85 (dd, J=10.9, 12.5 Hz, 1H), 2.73 (dd, J=10.5, 12.5 Hz, 1H), 2.61-2.50 (m, 2H), 1.80 (ddd, J=4.2, 11.2, 15.2 Hz, 2H), 1.46 (s, 3H), 1.35 (d, J=6.2 Hz, 3H).

Example 20

Cis-(2R,6R)-4-(7-cyanopyrazolo[1,5-a]pyridin-4-yl)-N-(4-hydroxycyclohexyl)-6-methyl-morpholine-2-carboxamide

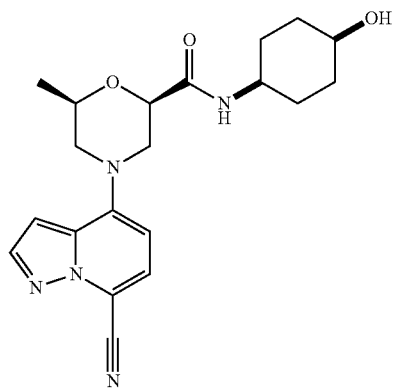

The title compound was prepared in analogy to the preparation of Example 4 by using cis-4-aminocyclohexanol (CAS: 56239-26-0, Pharmablock) instead of tetrahydropyran-4-amine (compound 4a). Example 20 (11 mg) was obtained as a white powder. MS: calc'd 384 (MH$^+$), measured 384 (MH$^+$). $^1$H NMR (400 MHz, METHANOL-d$_4$) δ 8.05 (d, J=2.4 Hz, 1H), 7.48 (d, J=7.9 Hz, 1H), 6.92 (d, J=2.4 Hz, 1H), 6.63 (d, J=8.1 Hz, 1H), 4.33 (dd, J=2.7, 10.9 Hz, 1H), 4.09 (td, J=2.3, 12.4 Hz, 1H), 4.05-3.96 (m, 1H), 3.87 (br s, 1H), 3.84-3.70 (m, 2H), 2.81 (dd, J=10.9, 12.3 Hz, 1H), 2.73 (dd, J=10.4, 12.5 Hz, 1H), 1.82-1.58 (m, 8H), 1.35 (d, J=6.2 Hz, 3H).

Example 21

Trans-(2R,6R)-4-(7-cyanopyrazolo[1,5-a]pyridin-4-yl)-N-(4-hydroxycyclohexyl)-6-methyl-morpholine-2-carboxamide

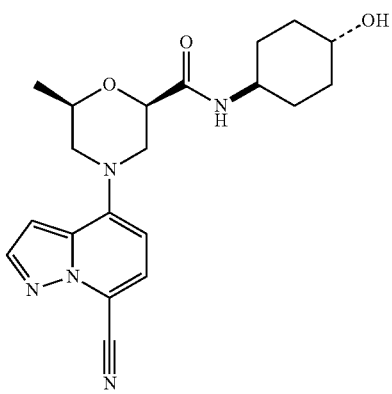

The title compound was prepared in analogy to the preparation of Example 4 by using trans-4-aminocyclohexanol (CAS: 50910-54-8, Pharmablock) instead of tetrahydropyran-4-amine (compound 4a). Example 21 (13 mg) was obtained as a white powder. MS: calc'd 384 (MH$^+$), measured 384 (MH$^+$). $^1$H NMR (400 MHz, METHANOL-d$_4$) δ 8.04 (d, J=2.4 Hz, 1H), 7.48 (d, J=7.9 Hz, 1H), 6.91 (d, J=2.4 Hz, 1H), 6.63 (d, J=7.9 Hz, 1H), 4.30 (dd, J=2.7, 10.9 Hz, 1H), 4.08 (td, J=2.3, 12.5 Hz, 1H), 4.04-3.94 (m, 1H), 3.79-3.65 (m, 2H), 3.60-3.50 (m, 1H), 2.79 (dd, J=10.9, 12.3 Hz, 1H), 2.71 (dd, J=10.5, 12.4 Hz, 1H), 2.01-1.84 (m, 4H), 1.48-1.27 (m, 7H).

Example 22

Endo-(2R,6R)-4-(7-cyanopyrazolo[1,5-a]pyridin-4-yl)-6-methyl-N-[3-oxa-9-azabicyclo[3.3.1]nonan-7-yl]morpholine-2-carboxamide

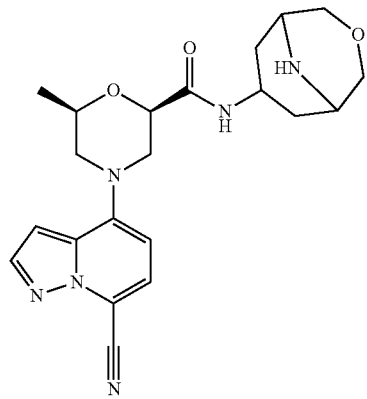 [SMILES: C[C@@H]1CN(c2ccc(C#N)n3nccc23)C[C@H](C(=O)NC2CC3COCC(C2)N3)O1]

The title compound was prepared in analogy to the preparation of Example 2 by using endo-tert-butyl 7-amino-3-oxa-9-azabicyclo[3.3.1]nonane-9-carboxylate (CAS: 280762-03-0, Pharmablock) instead of (3S,4R)-tert-butyl 3-amino-4-fluoropyrrolidine-1-carboxylate (compound 2c). Example 22 (9 mg) was obtained as a white powder. MS: calc'd 411 (MH$^+$), measured 411 (MH$^+$). $^1$H NMR (400 MHz, METHANOL-d$_4$) δ 8.05 (d, J=2.4 Hz, 1H), 7.48 (d, J=7.9 Hz, 1H), 6.92 (d, J=2.4 Hz, 1H), 6.63 (d, J=8.1 Hz, 1H), 4.45 (t, J=6.9 Hz, 1H), 4.32 (dd, J=2.8, 10.8 Hz, 1H), 4.14 (td, J=2.3, 12.4 Hz, 1H), 4.04-3.94 (m, 1H), 3.93-3.87 (m, 2H), 3.87-3.79 (m, 2H), 3.74 (br d, J=12.5 Hz, 1H), 2.92 (br s, 2H), 2.78 (dd, J=10.8, 12.4 Hz, 1H), 2.70 (dd, J=10.5, 12.4 Hz, 1H), 2.38-2.26 (m, 2H), 1.67 (br t, J=16.0 Hz, 2H), 1.30 (d, J=6.2 Hz, 3H).

Example 23

Exo-(2R,6R)-N-[8-azabicyclo[3.2.1]octan-3-yl]-4-(7-cyanopyrazolo[1,5-a]pyridin-4-yl)-6-methyl-morpholine-2-carboxamide

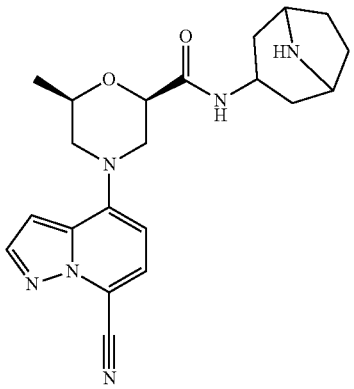 [SMILES: C[C@@H]1CN(c2ccc(C#N)n3nccc23)C[C@H](C(=O)NC2CC3CCC(C2)N3)O1]

The title compound was prepared in analogy to the preparation of Example 2 by using exo-tert-butyl 3-amino-8-azabicyclo[3.2.1]octane-8-carboxylate (CAS: 744183-20-8, Pharmablock) instead of (3S,4R)-tert-butyl 3-amino-4-fluoropyrrolidine-1-carboxylate (compound 2c). Example 23 (7 mg) was obtained as a white powder. MS: calc'd 395 (MH$^+$), measured 395 (MH$^+$). $^1$H NMR (400 MHz, METHANOL-d$_4$) δ 8.05 (d, J=2.3 Hz, 1H), 7.48 (d, J=7.9 Hz, 1H), 6.90 (d, J=2.4 Hz, 1H), 6.63 (d, J=8.1 Hz, 1H), 4.35 (dd, J=2.6, 10.8 Hz, 1H), 4.32-4.23 (m, 1H), 4.13-4.05 (m, 3H), 4.05-3.95 (m, 1H), 3.75 (br d, J=12.5 Hz, 1H), 2.80 (dd, J=10.8, 12.4 Hz, 1H), 2.71 (dd, J=10.5, 12.4 Hz, 1H), 2.19-2.00 (m, 6H), 1.93-1.82 (m, 2H), 1.35 (d, J=6.2 Hz, 3H).

Example 24

(2R,6R)-4-(7-cyanopyrazolo[1,5-a]pyridin-4-yl)-6-methyl-N-(4-piperidyl)morpholine-2-carboxamide

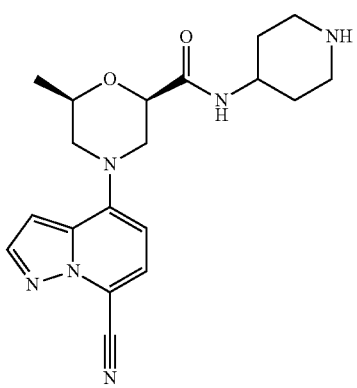 [SMILES: C[C@@H]1CN(c2ccc(C#N)n3nccc23)C[C@H](C(=O)NC2CCNCC2)O1]

The title compound was prepared in analogy to the preparation of Example 2 by using tert-butyl 4-aminopiperidine-1-carboxylate instead of (3S,4R)-tert-butyl 3-amino-4-fluoropyrrolidine-1-carboxylate (compound 2c). Example 24 (15 mg) was obtained as a white powder. MS: calc'd 369 (MH$^+$), measured 369 (MH$^+$). $^1$H NMR (400 MHz, METHANOL-d$_4$) δ 8.05 (d, J=2.4 Hz, 1H), 7.48 (d, J=7.9 Hz, 1H), 6.91 (d, J=2.6 Hz, 1H), 6.63 (d, J=7.9 Hz, 1H), 4.33 (dd, J=2.7, 10.9 Hz, 1H), 4.13-4.06 (m, 1H), 4.05-3.95 (m, 1H), 3.86 (tt, J=4.2, 11.2 Hz, 1H), 3.78-3.72 (m, 1H), 3.12-3.03 (m, 2H), 2.85-2.75 (m, 1H), 2.74-2.64 (m, 3H), 1.86 (br t, J=12.0 Hz, 2H), 1.58-1.45 (m, 2H), 1.35 (d, J=6.2 Hz, 3H).

Example 25

(2R,6R)-4-(7-cyanopyrazolo[1,5-a]pyridin-4-yl)-6-methyl-N-pyrrolidin-3-yl-morpholine-2-carboxamide

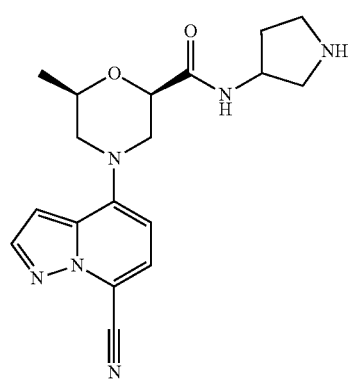 [SMILES: C[C@@H]1CN(c2ccc(C#N)n3nccc23)C[C@H](C(=O)NC2CCNC2)O1]

The title compound was prepared in analogy to the preparation of Example 2 by using tert-butyl 3-aminopyrrolidine-1-carboxylate instead of (3S,4R)-tert-butyl 3-amino-4-fluoropyrrolidine-1-carboxylate (compound 2c). Example 25 (9 mg) was obtained as a white powder. MS: calc'd 355 (MH$^+$), measured 355 (MH$^+$). $^1$H NMR (400 MHz, METHANOL-d$_4$) δ 8.05 (d, J=2.4 Hz, 1H), 7.48 (d, J=7.9 Hz, 1H), 6.91 (d, J=2.4 Hz, 1H), 6.63 (d, J=7.9 Hz, 1H), 4.43-4.36 (m, 1H), 4.34 (dd, J=2.7, 10.9 Hz, 1H), 4.13-4.06 (m, 1H), 4.05-3.95 (m, 1H), 3.75 (br d, J=12.5 Hz, 1H), 3.19-3.08 (m, 2H), 2.96 (ddd, J=6.7, 8.2, 11.3 Hz, 1H), 2.87-2.77 (m, 2H), 2.72 (dd, J=10.5, 12.4 Hz, 1H), 2.25-2.14 (m, 1H), 1.79 (dt, J=7.3, 12.9 Hz, 1H), 1.35 (d, J=6.4 Hz, 3H).

Example 26

(2R,6R)-N-(3-azabicyclo[3.2.1]octan-8-yl)-4-(7-cyanopyrazolo[1,5-a]pyridin-4-yl)-6-methyl-morpholine-2-carboxamide

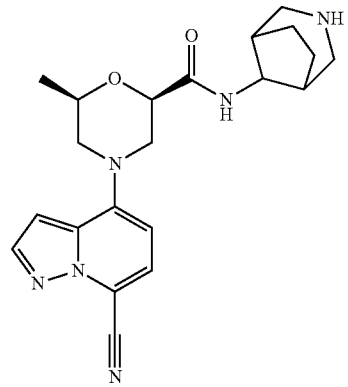 [SMILES: C[C@@H]1CN(c2ccc(C#N)n3nccc23)C[C@H](C(=O)NC2C3CCC2CNC3)O1]

The title compound was prepared in analogy to the preparation of Example 2 by using tert-butyl 8-amino-3-azabicyclo[3.2.1]octane-3-carboxylate (CAS: 1330763-51-3, Pharmablock) instead of (3S,4R)-tert-butyl 3-amino-4-fluoropyrrolidine-1-carboxylate (compound 2c). Example 26 (16 mg) was obtained as a white powder. MS: calc'd 395 (MH$^+$), measured 395 (MH$^+$). $^1$H NMR (400 MHz, METHANOL-d$_4$) δ 8.09-8.02 (m, 1H), 7.53-7.45 (m, 1H), 6.94-6.87 (m, 1H), 6.68-6.60 (m, 1H), 4.48-4.33 (m, 1H), 4.14-3.95 (m, 2H), 3.81-3.71 (m, 2H), 3.36 (s, 1H), 3.30-3.21 (m, 2H), 3.06 (br d, J=13.0 Hz, 1H), 2.94-2.80 (m, 1H), 2.79-2.68 (m, 1H), 2.67-2.51 (m, 2H), 2.14-2.03 (m, 2H), 1.83 (br d, J=8.7 Hz, 2H), 1.40-1.31 (m, 3H).

Example 27

(2R,6R)-4-(7-cyanopyrazolo[1,5-a]pyridin-4-yl)-6-methyl-N-(3-oxa-7-azabicyclo[3.3.1]nonan-9-yl)morpholine-2-carboxamide

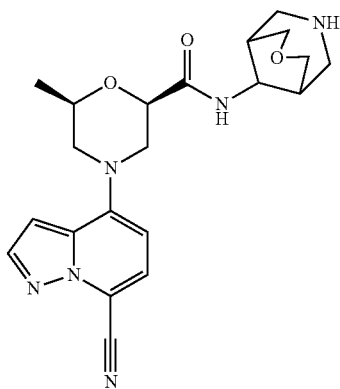 [SMILES: C[C@@H]1CN(c2ccc(C#N)n3nccc23)C[C@H](C(=O)NC2C3CNCC2COC3)O1]

The title compound was prepared in analogy to the preparation of Example 2 by using tert-butyl 9-amino-3-oxa-7-azabicyclo[3.3.1]nonane-7-carboxylate (CAS: 1251015-74-3, Wuxi Apptec) instead of (3S,4R)-tert-butyl 3-amino-4-fluoropyrrolidine-1-carboxylate (compound 2c). Example 27 (15 mg) was obtained as a white powder. MS: calc'd 411 (MH+), measured 411 (MH+). $^1$H NMR (400 MHz, METHANOL-d$_4$) δ 8.05 (d, J=2.3 Hz, 1H), 7.48 (d, J=7.9 Hz, 1H), 6.91 (d, J=2.4 Hz, 1H), 6.64 (dd, J=1.0, 8.0 Hz, 1H), 4.43 (td, J=3.1, 10.9 Hz, 1H), 4.23-4.13 (m, 1H), 4.13-4.01 (m, 3H), 4.01-3.88 (m, 3H), 3.82-3.71 (m, 1H), 3.35 (s, 1H), 3.22-3.03 (m, 3H), 2.88 (ddd, J=3.1, 10.8, 12.5 Hz, 1H), 2.80-2.70 (m, 1H), 1.81-1.71 (m, 2H), 1.36 (dd, J=2.7, 6.2 Hz, 3H).

Example 28

4-[(2R,6R)-2-(3,9-diazaspiro[5.5]undecane-3-carbonyl)-6-methyl-morpholin-4-yl]pyrazolo[1,5a]pyridine-7-carbonitrile

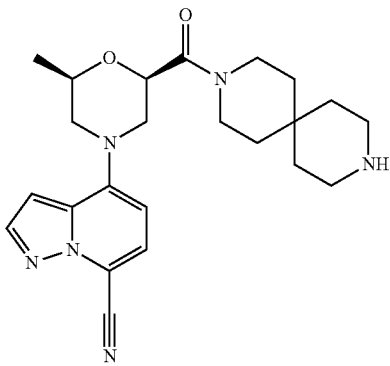 [SMILES: C[C@@H]1CN(c2ccc(C#N)n3nccc23)C[C@H](C(=O)N2CCC3(CCNCC3)CC2)O1]

The title compound was prepared in analogy to the preparation of Example 2 by using tert-butyl 3,9-diazaspiro[5.5]undecane-3-carboxylate instead of (3S,4R)-tert-butyl 3-amino-4-fluoropyrrolidine-1-carboxylate (compound 2c). Example 28 (20 mg) was obtained as a white powder. MS: calc'd 423 (MH+), measured 423 (MH+). $^1$H NMR (400 MHz, METHANOL-d$_4$) δ 8.03 (d, J=2.4 Hz, 1H), 7.48 (d, J=7.9 Hz, 1H), 6.88 (d, J=2.4 Hz, 1H), 6.65 (d, J=8.1 Hz, 1H), 4.64 (dd, J=2.6, 10.4 Hz, 1H), 4.07-3.96 (m, 1H), 3.85 (br d, J=12.7 Hz, 1H), 3.80-3.68 (m, 3H), 3.63-3.53 (m, 1H), 3.53-3.43 (m, 1H), 3.24-3.17 (m, 4H), 3.12 (dd, J=10.5, 12.8 Hz, 1H), 2.71 (dd, J=10.5, 12.4 Hz, 1H), 1.87-1.72 (m, 4H), 1.71-1.59 (m, 3H), 1.59-1.50 (m, 1H), 1.29 (d, J=6.2 Hz, 3H).

Example 29

(2R,6R)-4-(7-cyanopyrazolo[1,5-a]pyridin-4-yl)-6-methyl-N-(4-pyridyl)morpholine-2-carboxamide

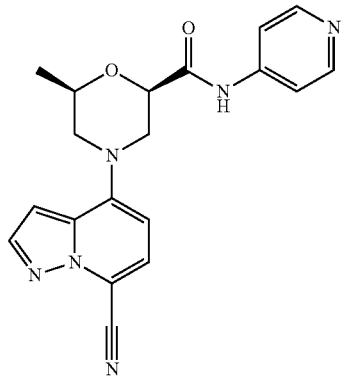 [SMILES: C[C@@H]1CN(c2ccc(C#N)n3nccc23)C[C@H](C(=O)Nc2ccncc2)O1]

The title compound was prepared in analogy to the preparation of Example 4 by using pyridine-4-amine instead of tetrahydropyran-4-amine (compound 4a). Example 29 (24 mg) was obtained as a light yellow powder. MS: calc'd 363 (MH+), measured 363 (MH+). $^1$H NMR (400 MHz, METHANOL-d$_4$) δ 8.67 (d, J=7.3 Hz, 2H), 8.36 (d, J=7.3 Hz, 2H), 8.07 (d, J=2.4 Hz, 1H), 7.50 (d, J=7.9 Hz, 1H), 6.92 (d, J=2.4 Hz, 1H), 6.68 (d, J=7.9 Hz, 1H), 4.64 (dd, J=2.8, 10.7 Hz, 1H), 4.20-4.06 (m, 2H), 3.81 (td, J=2.1, 12.5 Hz, 1H), 3.01 (dd, J=10.8, 12.4 Hz, 1H), 2.78 (dd, J=10.5, 12.5 Hz, 1H), 1.42 (d, J=6.2 Hz, 3H).

Example 30

(2R,6R)-4-(7-cyanopyrazolo[1,5-a]pyridin-4-yl)-6-methyl-N-(1-methylpyrazol-3-yl)morpholine-2-carboxamide

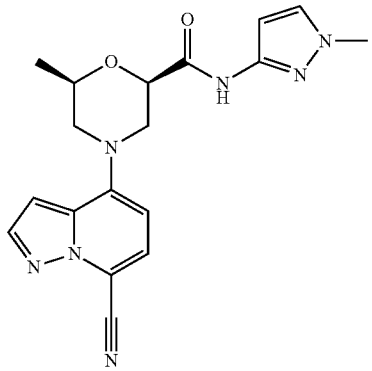 [SMILES: C[C@@H]1CN(c2ccc(C#N)n3nccc23)C[C@H](C(=O)Nc2ccn(C)n2)O1]

The title compound was prepared in analogy to the preparation of Example 4 by using 1-methylpyrazol-3-amine instead of tetrahydropyran-4-amine (compound 4a). Example 30 (10 mg) was obtained as a light yellow powder. MS: calc'd 366 (MH$^+$), measured 366 (MH$^+$). $^1$H NMR (400 MHz, METHANOL-d$_4$) δ 8.06 (d, J=2.4 Hz, 1H), 7.51-7.45 (m, 2H), 6.93 (d, J=2.4 Hz, 1H), 6.66 (d, J=8.1 Hz, 1H), 6.54 (d, J=2.3 Hz, 1H), 4.50 (dd, J=2.8, 10.9 Hz, 1H), 4.16 (td, J=2.4, 12.4 Hz, 1H), 4.13-4.03 (m, 1H), 3.81 (s, 3H), 3.80-3.75 (m, 1H), 2.92 (dd, J=10.9, 12.5 Hz, 1H), 2.77 (dd, J=10.5, 12.5 Hz, 1H), 1.39 (d, J=6.2 Hz, 3H).

Example 31

Trans-(2R,6R)-N-(3-azabicyclo[3.1.0]hexan-6-yl)-4-(7-cyanopyrazolo[1,5-a]pyridin-4-yl)-6-methyl-morpholine-2-carboxamide The title compound was prepared in analogy to the preparation of Example 2 by using trans-tert-butyl 6-amino-3-azabicyclo[3.1.0]hexane-3-carboxylate (CAS: 273206-92-1, Pharmablock) instead of (3S,4R)-tert-butyl 3-amino-4-fluoropyrrolidine-1-carboxylate (compound 2c). Example 31 (20 mg) was obtained as a white powder. MS: calc'd 367 (MH$^+$), measured 367 (MH$^+$). $^1$H NMR (400 MHz, METHANOL-d$_4$) δ 8.05 (d, J=2.3 Hz, 1H), 7.48 (d, J=7.9 Hz, 1H), 6.90 (d, J=2.4 Hz, 1H), 6.62 (d, J=8.1 Hz, 1H), 4.34 (dd, J=2.7, 10.8 Hz, 1H), 4.08 (td, J=2.2, 12.4 Hz, 1H), 4.03-3.93 (m, 1H), 3.77-3.70 (m, 1H), 3.51-3.44 (m, 2H), 3.43-3.36 (m, 2H), 2.79 (dd, J=10.9, 12.3 Hz, 1H), 2.70 (dd, J=10.5, 12.4 Hz, 1H), 2.62 (t, J=2.4 Hz, 1H), 2.04 (br d, J=2.3 Hz, 2H), 1.33 (d, J=6.2 Hz, 3H).

Example 32

(2R,6R)-4-(7-cyanopyrazolo[1,5-a]pyridin-4-yl)-6-methyl-N-(5-methyl-5-azaspiro[2.4]heptan-7-yl)morpholine-2-carboxamide

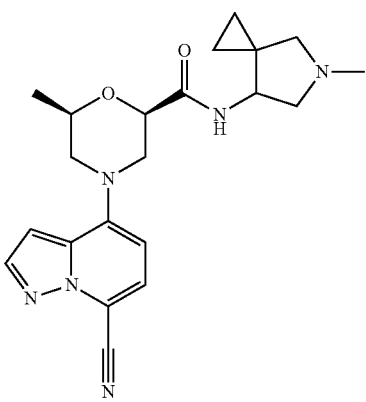 [SMILES: C[C@@H]1CN(c2ccc(C#N)n3nccc23)C[C@H](C(=O)NC2CN(C)CC23CC3)O1]

The title compound was prepared according to the following scheme:

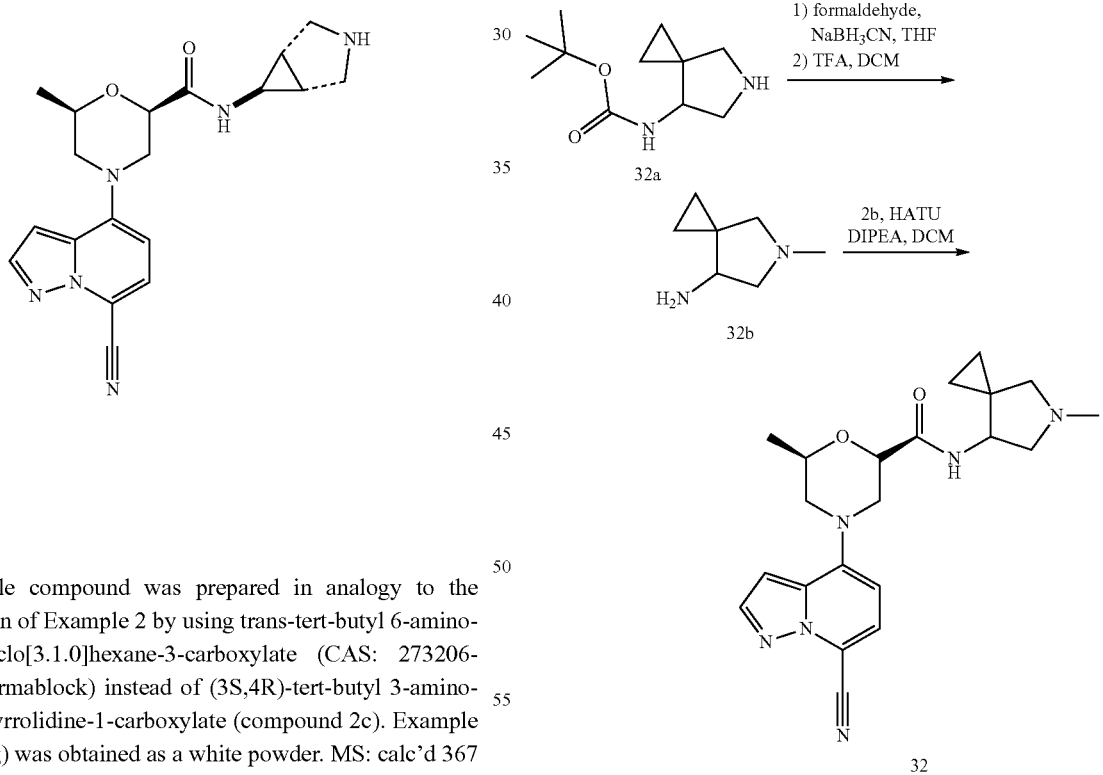

Step 1: preparation of 5-methyl-5-azaspiro[2.4]heptan-7-amine (Compound 32b)

To a solution of tert-butyl 5-azaspiro[2.4]heptan-7-ylcarbamate (106 mg, 0.50 mmol) in THF (3 mL) was added formaldehyde (13 M in H$_2$O, 2 mL, 26 mmol). The mixture was stirred at rt for 1 h, then NaBH₃CN (63 mg, 1.0 mmol) was added. The reaction mixture was stirred at rt for another 1 h, then THF was removed under reduced pressure. The residue was diluted with water, and extracted with DCM. The organic layer was washed with brine, dried over Na₂SO₄ and concentrated to give an oil which was purified by column chromatography to give a colorless oil (100 mg). The oil was dissolved in DCM (2 mL) and treated with TFA (1 mL, 13 mmol). The mixture was stirred at rt for 1 h, then concentrated to give a crude compound 32b (100 mg) as an yellowish oil which is directly used in next step. MS: calc'd 127 (MH⁺), measured 127 (MH⁺).

Step 2: preparation of (2R,6R)-4-(7-cyanopyrazolo [1,5-a]42yridine-4-yl)-6-methyl-N-(5-methyl-5-azaspiro[2.4]heptan-7-yl)morpholine-2-carboxamide (Example 32)

To a solution of (2R,6R)-4-(7-cyanopyrazolo[1,5-a]pyridin-4-yl)-6-methyl-morpholine-2-carboxylic acid (2b, 30 mg, 0.10 mmol), 5-methyl-5-azaspiro[2.4]heptan-7-amine (32b, 20 mg, 0.16 mmol) and DIPEA (40 mg, 55 µL, 0.31 mmol) in DCM (3 mL) was added HATU (80 mg, 0.21 mmol). The reaction mixture was stirred at rt overnight, then diluted with DCM, washed with sat. NH₄Cl and brine, dried over Na₂SO₄, and concentrated to give a crude product which was purified by prep-HPLC to give Example 32 (8 mg) as a white powder. MS: calc'd 395 (MH⁺), measured 395 (MH⁺). ¹H NMR (400 MHz, METHANOL-d₄) δ 8.04 (d, J=2.4 Hz, 1H), 7.48 (d, J=8.1 Hz, 1H), 6.91 (d, J=2.4 Hz, 1H), 6.63 (dd, J=2.3, 8.1 Hz, 1H), 4.34 (ddd, J=2.7, 8.7, 11.0 Hz, 1H), 4.28-4.21 (m, 1H), 4.15-4.07 (m, 1H), 4.06-3.96 (m, 1H), 3.75 (dd, J=2.1, 12.5 Hz, 1H), 2.97 (ddd, J=4.0, 6.5, 10.3 Hz, 1H), 2.84-2.67 (m, 4H), 2.47 (d, J=9.3 Hz, 1H), 2.39 (d, J=2.0 Hz, 3H), 1.37 (d, J=6.2 Hz, 3H), 0.84-0.54 (m, 4H).

Example 33

(2R,6R)-4-(7-cyanopyrazolo[1,5-a]pyridin-4-yl)-6-methyl-N-(8-methyl-8-azabicyclo[3.2.1]octan-3-yl) morpholine-2-carboxamide

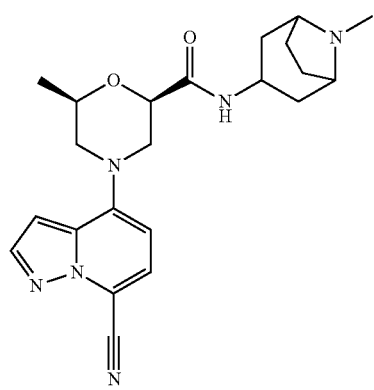 [SMILES: C[C@@H]1CN(c2ccc(C#N)n3nccc23)C[C@H](C(=O)NC2CC3CCC(C2)N3C)O1]

The title compound was prepared in analogy to the preparation of Example 4 by using 8-methyl-8-azabicyclo [3.2.1]octan-3-amine (CAS: 98998-25-5, Bepharm) instead of tetrahydropyran-4-amine (compound 4a). Example 33 (15 mg) was obtained as a white powder. MS: calc'd 409 (MH⁺), measured 409 (MH⁺). ¹H NMR (400 MHz, METHANOL-d₄) δ 8.04 (d, J=2.3 Hz, 1H), 7.50-7.44 (m, 1H), 6.93-6.88 (m, 1H), 6.66-6.59 (m, 1H), 4.38-4.28 (m, 1H), 4.23-3.94 (m, 3H), 3.79-3.70 (m, 1H), 3.24 (br d, J=8.3 Hz, 2H), 2.84-2.76 (m, 1H), 2.76-2.67 (m, 1H), 2.36-2.28 (m, 3H), 2.25-2.06 (m, 3H), 1.92-1.84 (m, 1H), 1.82-1.61 (m, 4H), 1.39-1.31 (m, 3H).

Example 34

(2R,6R)-4-(7-cyanopyrazolo[1,5-a]pyridin-4-yl)-6-methyl-N-(2-methyl-2-azabicyclo[2.2.2]octan-5-yl) morpholine-2-carboxamide

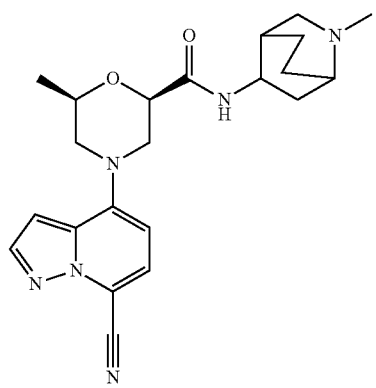 [SMILES: C[C@@H]1CN(c2ccc(C#N)n3nccc23)C[C@H](C(=O)NC2CC3CCC2CN3C)O1]

The title compound was prepared in analogy to the preparation of Example 4 by using 2-methyl-2-azabicyclo [2.2.2]octan-5-amine (CAS: 93798-12-0) instead of tetrahydropyran-4-amine (compound 4a). Example 34 (11 mg) was obtained as a white powder. MS: calc'd 409 (MH⁺), measured 409 (MH⁺). ¹H NMR (400 MHz, METHANOL-d₄) δ 8.04 (d, J=2.4 Hz, 1H), 7.47 (dd, J=1.3, 8.0 Hz, 1H), 6.94-6.89 (m, 1H), 6.63 (d, J=7.9 Hz, 1H), 4.39-4.31 (m, 1H), 4.16-3.96 (m, 3H), 3.75 (br d, J=12.2 Hz, 1H), 3.03-2.77 (m, 2H), 2.77-2.69 (m, 2H), 2.66 (br s, 1H), 2.54-2.42 (m, 1H), 2.42-2.35 (m, 3H), 2.13-1.94 (m, 1H), 1.91-1.76 (m, 2H), 1.76-1.63 (m, 1H), 1.62-1.51 (m, 1H), 1.51-1.41 (m, 1H), 1.40-1.33 (m, 3H).

Example 35

(2R,6R)-4-(7-cyanopyrazolo[1,5-a]pyridin-4-yl)-6-methyl-N-(9-methyl-9-azabicyclo[3.3.1]nonan-3-yl)morpholine-2-carboxamide

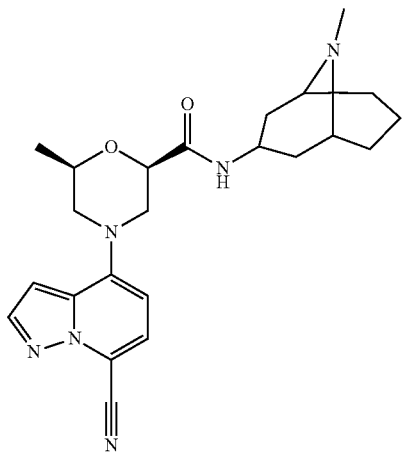 [SMILES: C[C@@H]1CN(c2ccc(C#N)n3nccc23)C[C@H](C(=O)NC2CC3CCCC34C(C2)N4C)O1]

The title compound was prepared according to the following scheme:

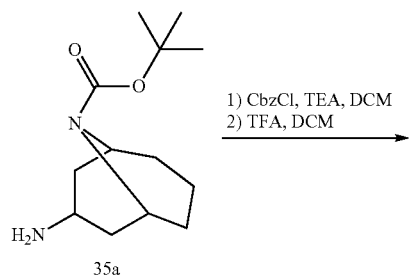

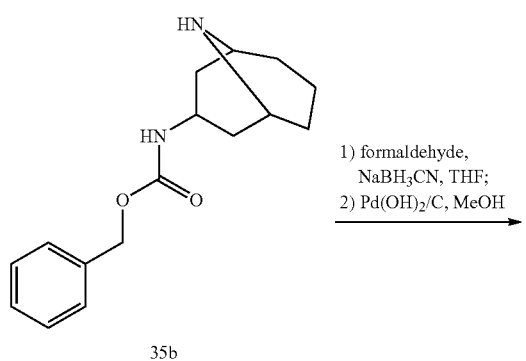

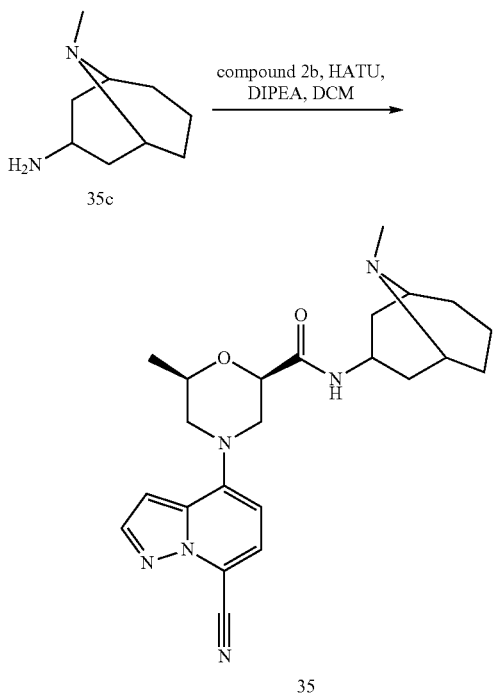

Step 1: preparation of benzyl N-(9-azabicyclo[3.3.1]nonan-3-yl)carbamate (Compound 35b)

To a solution of tert-butyl 3-amino-9-azabicyclo[3.3.1]nonane-9-carboxylate (CAS: 202797-03-3, Pharmablock) (240 mg, 1.0 mmol) and TEA (202 mg, 278 µL, 2.0 mmol) in DCM (6 mL) was added benzyl chloroformate (204 mg, 171 µL, 1.2 mmol) at 0° C. The mixture was stirred at rt overnight, then concentrated to give a crude oil which was purified by column chromatography to give a colorless oil (214 mg). The resulting oil was dissolved in DCM (2 mL), and treated with TFA (1 mL). The reaction mixture was stirred at rt for 2 h, then concentrated to give a crude oil (274 mg) which was directly used in next step. MS: calc'd 275 (MH$^+$), measured 275 (MH$^+$).

Step 2: preparation of 9-methyl-9-azabicyclo[3.3.1]nonan-3-amine (Compound 35c)

To a solution of benzyl 9-azabicyclo[3.3.1]nonan-3-ylcarbamate (35b, 274 mg, 1.0 mmol) in THF (5 mL) was added formaldehyde (13 M in H$_2$O, 5 mL, 65 mmol). The mixture was stirred at rt for 30 min, then NaBH$_3$CN (126 mg, 2 mmol) was added. The reaction mixture was stirred at rt overnight, then quenched with sat. NH$_4$Cl. THF was removed under reduced pressure, the residue was diluted with water, extracted with DCM. The organic layer was washed with brine, dried over Na$_2$SO$_4$, and concentrated to give an oil which was purified by column chromatography to give a white solid. The white solid was dissolved in MeOH (5 mL) to form a solution, to which Pd(OH)$_2$ (20% on carbon, wet) was added. The mixture was stirred at rt under H$_2$ balloon for 3 hrs, then filtered through celite. The filtrate was concentrated to give the crude compound 35c (100 mg) as a semisolid which was directly used in next step. MS: calc'd 155 (MH$^+$), measured 155 (MH$^+$).

Step 3: preparation of (2R,6R)-4-(7-cyanopyrazolo[1,5-a]45yridine-4-yl)-6-methyl-N-(9-methyl-9-azabicyclo[3.3.1]nonan-3-yl)morpholine-2-carboxamide (Example 35)

The title compound was prepared in analogy to the preparation of Example 4 by using 9-methyl-9-azabicyclo[3.3.1]nonan-3-amine (compound 37c) instead of tetrahydropyran-4-amine (compound 4a). Example 35 (15 mg) was obtained as a white powder. MS: calc'd 423 (MH⁺), measured 423 (MH⁺). ¹H NMR (400 MHz, METHANOL-d₄) δ 8.07 (d, J=2.2 Hz, 1H), 7.50 (d, J=8.1 Hz, 1H), 6.93 (d, J=2.2 Hz, 1H), 6.65 (d, J=8.1 Hz, 1H), 4.77 (tt, J=6.1, 12.2 Hz, 1H), 4.37 (dd, J=2.4, 10.8 Hz, 1H), 4.13 (br d, J=12.5 Hz, 1H), 4.08-3.97 (m, 1H), 3.77 (br d, J=12.2 Hz, 1H), 3.59 (br s, 2H), 3.03 (s, 3H), 2.86-2.67 (m, 2H), 2.33-2.16 (m, 4H), 2.16-1.91 (m, 5H), 1.88-1.73 (m, 1H), 1.38 (d, J=6.1 Hz, 3H).

Example 36

(2R,6R)-N-(2-azabicyclo[2.2.1]heptan-5-yl)-4-(7-cyanopyrazolo[1,5-a]pyridin-4-yl)-6-methyl-morpholine-2-carboxamide

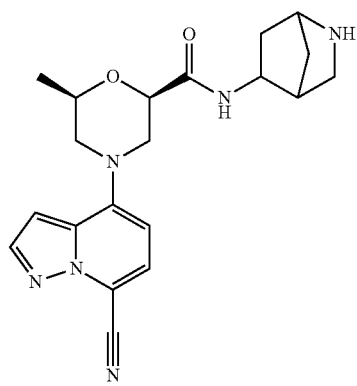 [SMILES: C[C@@H]1CN(c2ccc(C#N)n3nccc23)C[C@H](C(=O)NC2CC3CC2CN3)O1]

The title compound was prepared in analogy to the preparation of Example 2 by using tert-butyl 5-amino-2-azabicyclo[2.2.1]heptane-2-carboxylate (CAS: 207405-62-7, Bepharm) instead of (3S,4R)-tert-butyl 3-amino-4-fluoropyrrolidine-1-carboxylate (compound 2c). Example 36 (23 mg) was obtained as a white powder. MS: calc'd 381 (MH⁺), measured 381 (MH⁺). ¹H NMR (400 MHz, METHANOL-d₄) δ 8.05 (d, J=2.4 Hz, 1H), 7.48 (d, J=7.9 Hz, 1H), 6.90 (d, J=2.7 Hz, 1H), 6.64 (d, J=7.9 Hz, 1H), 4.44-4.23 (m, 2H), 4.15-4.05 (m, 2H), 4.04-3.94 (m, 1H), 3.80-3.71 (m, 1H), 3.40-3.34 (m, 1H), 3.23-3.08 (m, 1H), 3.07-2.92 (m, 1H), 2.88-2.79 (m, 1H), 2.77-2.67 (m, 1H), 2.38-2.20 (m, 1H), 2.06-1.95 (m, 1H), 1.91-1.80 (m, 1H), 1.79-1.56 (m, 1H), 1.36 (dd, J=6.2, 8.4 Hz, 3H).

Example 37

(2R,6R)-N-(3-azabicyclo[3.3.1]nonan-9-yl)-4-(7-cyanopyrazolo[1,5-a]pyridin-4-yl)-6-methyl-morpholine-2-carboxamide

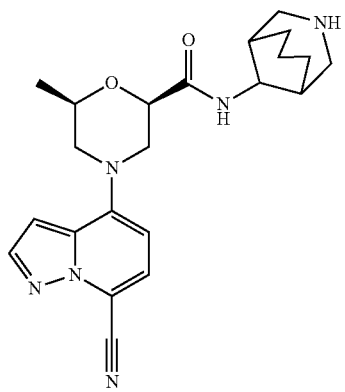 [SMILES: C[C@@H]1CN(c2ccc(C#N)n3nccc23)C[C@H](C(=O)NC2C3CCCC2CNC3)O1]

The title compound was prepared in analogy to the preparation of Example 2 by using tert-butyl 9-amino-3-azabicyclo[3.3.1]nonane-3-carboxylate (CAS: 1198466-20-4, Wuxi Apptec) instead of (3S,4R)-tert-butyl 3-amino-4-fluoropyrrolidine-1-carboxylate (compound 2c). Example 37 (19 mg) was obtained as a white powder. MS: calc'd 409 (MH⁺), measured 409 (MH⁺). ¹H NMR (400 MHz, METHANOL-d₄) δ 8.05 (d, J=2.4 Hz, 1H), 7.49 (d, J=7.9 Hz, 1H), 6.92 (d, J=2.4 Hz, 1H), 6.65 (d, J=8.1 Hz, 1H), 4.43 (dd, J=2.8, 10.8 Hz, 1H), 4.16-4.00 (m, 3H), 3.80-3.74 (m, 1H), 3.57-3.51 (m, 2H), 3.48-3.40 (m, 2H), 2.87 (dd, J=10.9, 12.5 Hz, 1H), 2.75 (dd, J=10.5, 12.5 Hz, 1H), 2.23 (br s, 2H), 1.96 (br d, J=4.9 Hz, 2H), 1.85-1.70 (m, 4H), 1.36 (d, J=6.2 Hz, 3H).

Example 38

(2R,6R)-4-(7-chloropyrazolo[1,5-a]pyridin-4-yl)-6-methyl-N-(1-methyl-4-piperidyl)morpholine-2-carboxamide

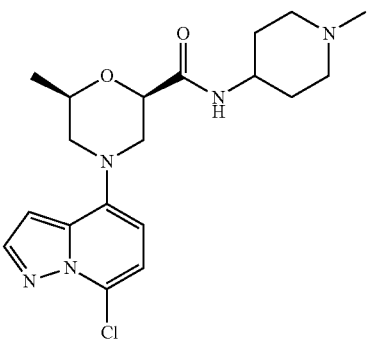 [SMILES: C[C@@H]1CN(c2ccc(Cl)n3nccc23)C[C@H](C(=O)NC2CCN(C)CC2)O1]

The title compound was prepared in analogy to the preparation of Example 1 by using 4-bromo-7-chloro-pyrazolo[1,5-a]pyridine (CAS: 1427419-42-8, Pharmablock) instead of 4-chloropyrazolo[1,5-a]pyridine-7-carbonitrile (compound 1d). Example 38 (2 mg) was obtained as a light yellow powder. MS: calc'd 392 (MH⁺), measured 392

(MH⁺). ¹H NMR (400 MHz, METHANOL-d₄) δ 8.04 (d, J=2.3 Hz, 1H), 6.98 (d, J=7.9 Hz, 1H), 6.85 (d, J=2.4 Hz, 1H), 6.68 (d, J=7.9 Hz, 1H), 4.34 (dd, J=2.6, 10.8 Hz, 1H), 4.07-3.96 (m, 1H), 3.89-3.82 (m, 1H), 3.82-3.70 (m, 1H), 3.55-3.46 (m, 1H), 2.90 (br d, J=10.3 Hz, 2H), 2.64 (d, J=10.9 Hz, 1H), 2.60-2.52 (m, 1H), 2.32 (s, 3H), 2.24-2.13 (m, 2H), 1.87 (br t, J=12.3 Hz, 2H), 1.72-1.57 (m, 2H), 1.34 (d, J=6.2 Hz, 3H).

Example 39

(2R,6R)-N-(3-amino-2,2-dimethyl-propyl)-4-(7-cyanopyrazolo[1,5-a]pyridin-4-yl)-6-methyl-morpholine-2-carboxamide

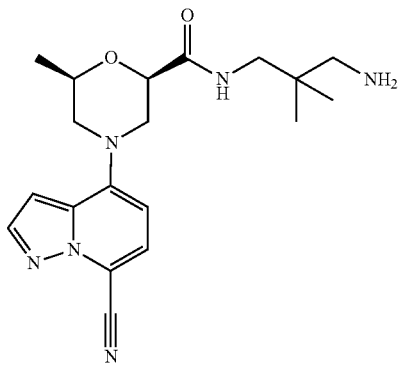 [SMILES: C[C@@H]1CN(c2ccc(C#N)n3nccc23)C[C@H](C(=O)NCC(C)(C)CN)O1]

The title compound was prepared in analogy to the preparation of Example 2 by using tert-butyl N-(3-amino-2,2-dimethyl-propyl)carbamate instead of (3S,4R)-tert-butyl 3-amino-4-fluoropyrrolidine-1-carboxylate (compound 2c). Example 39 (17 mg) was obtained as a white powder. MS: calc'd 371 (MH⁺), measured 371 (MH⁺). ¹H NMR (400 MHz, METHANOL-d₄) δ 8.05 (d, J=2.4 Hz, 1H), 7.48 (d, J=8.1 Hz, 1H), 6.92 (d, J=2.6 Hz, 1H), 6.63 (d, J=7.9 Hz, 1H), 4.38 (dd, J=2.8, 10.8 Hz, 1H), 4.12 (td, J=2.2, 12.4 Hz, 1H), 4.07-3.96 (m, 1H), 3.78-3.70 (m, 1H), 3.20-3.06 (m, 2H), 2.81 (dd, J=10.9, 12.4 Hz, 1H), 2.74 (dd, J=10.5, 12.5 Hz, 1H), 2.41 (s, 2H), 1.36 (d, J=6.2 Hz, 3H), 0.92 (s, 6H).

Example 40

(2R,6R)-4-(7-cyanopyrazolo[1,5-a]pyridin-4-yl)-6-methyl-N-(pyrrolidin-3-ylmethyl)morpholine-2-carboxamide

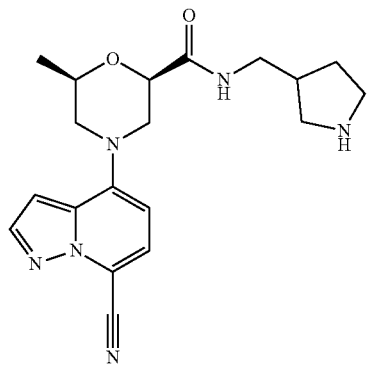 [SMILES: C[C@@H]1CN(c2ccc(C#N)n3nccc23)C[C@H](C(=O)NCC2CCNC2)O1]

The title compound was prepared in analogy to the preparation of Example 2 by using tert-butyl 3-(aminomethyl)pyrrolidine-1-carboxylate instead of (3S,4R)-tert-butyl 3-amino-4-fluoropyrrolidine-1-carboxylate (compound 2c). Example 40 (19 mg) was obtained as a light yellow solid. MS: calc'd 369 (MH⁺), measured 369 (MH⁺). ¹H NMR (400 MHz, METHANOL-d₄) δ 8.05 (d, J=2.4 Hz, 1H), 7.47 (d, J=7.9 Hz, 1H), 6.91 (d, J=2.4 Hz, 1H), 6.63 (d, J=8.1 Hz, 1H), 4.37 (dd, J=2.6, 10.8 Hz, 1H), 4.12 (br d, J=12.5 Hz, 1H), 4.06-3.95 (m, 1H), 3.74 (br d, J=12.3 Hz, 1H), 3.43-3.33 (m, 4H), 3.28-3.21 (m, 1H), 3.00 (dd, J=8.3, 11.6 Hz, 1H), 2.84-2.76 (m, 1H), 2.72 (dd, J=10.5, 12.3 Hz, 1H), 2.62 (td, J=7.5, 15.1 Hz, 1H), 2.20-2.09 (m, 1H), 1.83-1.70 (m, 1H), 1.35 (d, J=6.2 Hz, 3H).

Example 41

(2R,6R)-N-(2-amino-1,1-dimethyl-ethyl)-4-(7-cyanopyrazolo[1,5-a]pyridin-4-yl)-6-methyl-morpholine-2-carboxamide

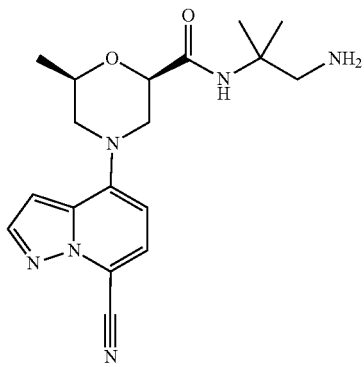 [SMILES: C[C@@H]1CN(c2ccc(C#N)n3nccc23)C[C@H](C(=O)NC(C)(C)CN)O1]

The title compound was prepared in analogy to the preparation of Example 2 by using tert-butyl N-(2-amino-2-methyl-propyl)carbamate instead of (3S,4R)-tert-butyl 3-amino-4-fluoropyrrolidine-1-carboxylate (compound 2c). Example 41 (14 mg) was obtained as a light yellow solid. MS: calc'd 357 (MH⁺), measured 357 (MH⁺). ¹H NMR (400 MHz, METHANOL-d₄) δ 8.05 (d, J=2.3 Hz, 1H), 7.49 (d, J=7.9 Hz, 1H), 6.89 (d, J=2.4 Hz, 1H), 6.64 (d, J=8.1 Hz, 1H), 4.34 (dd, J=2.8, 10.8 Hz, 1H), 4.08 (td, J=2.2, 12.5 Hz, 1H), 4.05-3.97 (m, 1H), 3.79-3.72 (m, 1H), 3.41-3.34 (m, 1H), 3.28-3.21 (m, 1H), 2.86 (dd, J=10.9, 12.5 Hz, 1H), 2.73 (dd, J=10.5, 12.5 Hz, 1H), 1.45 (s, 3H), 1.44 (s, 3H), 1.35 (d, J=6.2 Hz, 3H).

Example 42

(2R,6R)-4-(7-cyanopyrazolo[1,5-a]pyridin-4-yl)-6-methyl-N-[4-(piperazine-1-carbonyl)phenyl]morpholine-2-carboxamide

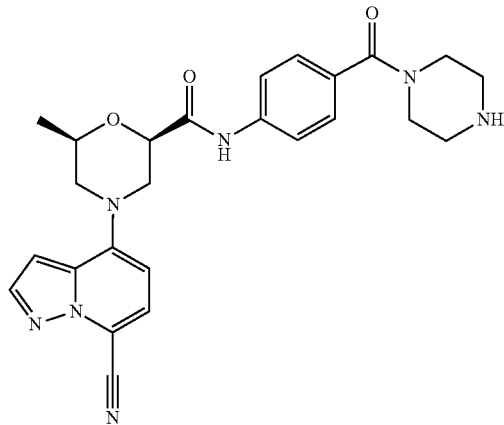 [SMILES: C[C@@H]1CN(c2ccc(C#N)n3nccc23)C[C@H](C(=O)Nc2ccc(C(=O)N3CCNCC3)cc2)O1]

The title compound was prepared in analogy to the preparation of Example 2 by using tert-butyl 4-(4-aminobenzoyl)piperazine-1-carboxylate instead of (3S,4R)-tert-butyl 3-amino-4-fluoropyrrolidine-1-carboxylate (compound 2c). Example 42 (15 mg) was obtained as a white solid. MS: calc'd 474 (M+), measured 474 (MH+). $^1$H NMR (400 MHz, METHANOL-$d_4$) δ 8.06 (d, J=2.4 Hz, 1H), 7.80-7.72 (m, 2H), 7.49 (d, J=7.9 Hz, 1H), 7.45-7.39 (m, 2H), 6.93 (d, J=2.4 Hz, 1H), 6.66 (d, J=7.9 Hz, 1H), 4.51 (dd, J=2.7, 10.8 Hz, 1H), 4.21-4.13 (m, 1H), 4.13-4.03 (m, 1H), 3.79 (br d, J=12.5 Hz, 1H), 3.76-3.38 (m, 4H), 2.96 (dd, J=10.9, 12.4 Hz, 1H), 2.85 (br s, 3H), 2.78 (dd, J=10.5, 12.5 Hz, 2H), 1.41 (d, J=6.2 Hz, 3H).

Example 43

4-[(3R,5S)-3-amino-5-methyl-1-piperidyl]pyrazolo[1,5-a]pyridine-7-carbonitrile

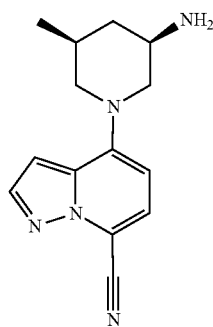 [SMILES: C[C@H]1C[C@@H](N)CN(c2ccc(C#N)n3nccc23)C1]

The title compound was prepared according to the following scheme:

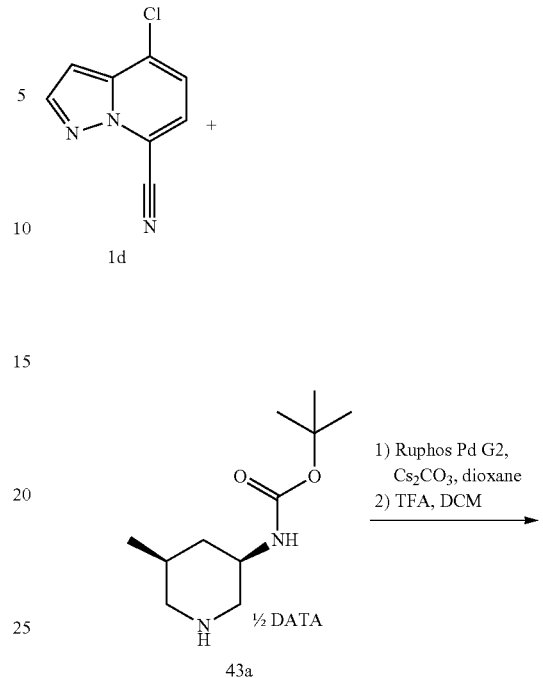

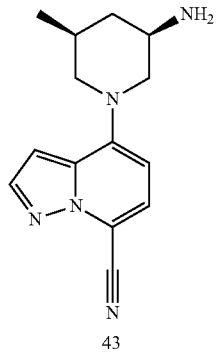

A solution of 4-chloropyrazolo[1,5-a]pyridine-7-carbonitrile (compound 1d, 25 mg, 141 μmol), tert-butyl N-[(3R,5S)-5-methyl-3-piperidyl]carbamate hemi((2S,3S)-2,3-bis((4-methoxybenzoyl)oxy)succinate) (Reference: WO 2015057655 A1) (compound 45a, 71 mg, 84 μmol), Cs$_2$CO$_3$ (183 mg, 0.56 mmol) in 1,4-dioxane (3 mL) was bubbled with N$_2$ for 5 min, then Ruphos Pd G2 (10.9 mg, 14 μmol) was added. The mixture was heated at 90° C. (oil bath) under N$_2$ for 5 h, then cooled to rt and diluted with EtOAc, and filtered through celite. The filtrate was concentrated to give a brown oil, which was dissolved in DCM (2 mL) to form a solution. To the solution was added TFA (1 mL) and the reaction mixture was stirred at rt for 1 h, then concentrated to give a crude product which was purified by prep-HPLC to give Example 43 (13 mg) as a grey powder. MS: calc'd 256 (MH+), measured 256 (MH+). $^1$H NMR (400 MHz, METHANOL-$d_4$) δ 8.03 (d, J=2.3 Hz, 1H), 7.46 (d, J=8.1 Hz, 1H), 6.84 (d, J=2.4 Hz, 1H), 6.63 (d, J=8.1 Hz, 1H), 4.20-4.12 (m, 1H), 3.86-3.76 (m, 1H), 3.53 (tt, J=4.1, 11.5 Hz, 1H), 2.81 (t, J=11.5 Hz, 1H), 2.55 (t, J=11.9 Hz, 1H), 2.27 (br d, J=12.3 Hz, 1H), 2.11-1.98 (m, 1H), 1.28 (q, J=12.0 Hz, 1H), 1.08 (d, J=6.7 Hz, 3H).

Example 44

(2S)-2-amino-N-[(3R,5S)-1-(7-cyanopyrazolo[1,5-a]pyridin-4-yl)-5-methyl-3-piperidyl]propanamide

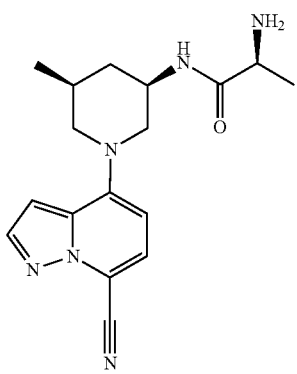 [SMILES: C[C@H]1C[C@@H](NC(=O)[C@H](C)N)CN(c2ccc(C#N)n3nccc23)C1]

The title compound was prepared according to the following scheme:

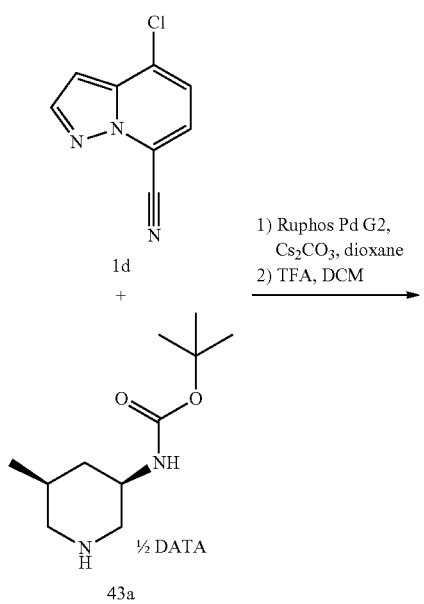

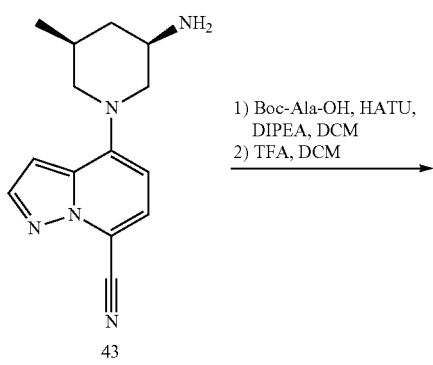

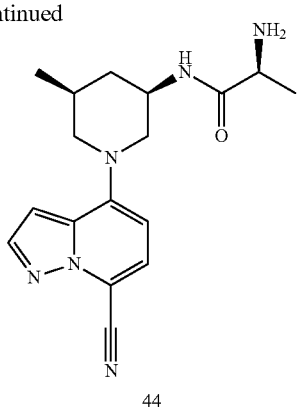

44

Step 1: Preparation of 4-[(3R,5S)-3-amino-5-methyl-1-piperidyl]pyrazolo[1,5-a]pyridine-7-carbonitrile (Example 43)

A solution of 4-chloropyrazolo[1,5-a]pyridine-7-carbonitrile (1d, 200 mg, 1.13 mmol), tert-butyl N-[(3R,5S)-5-methyl-3-piperidyl]carbamate hemi((2S,3S)-2,3-bis((4-methoxybenzoyl)oxy)succinate) (Reference: WO 2015057655 A1) (compound 43a, 525 mg, 619 µmol), $Cs_2CO_3$ (1.47 g, 4.5 mmol) in 1,4-dioxane (15 mL) was bubbled with $N_2$ for 5 min, then Ruphos Pd G2 (61 mg, 79 µmol) was added. The mixture was heated at 90° C. (oil bath) under $N_2$ for 5 h, then cooled to rt and diluted with EtOAc, and filtered through celite. The filtrate was concentrated to give a brown oil, which was dissolved in DCM (2 mL) to form a solution. To the solution was added TFA (1 mL) and the mixture was stirred at rt for 1 h, then concentrated to give a crude Example 43 (500 mg) which was directly used in next step.

Step 2: preparation of (2S)-2-amino-N-[(3R,5S)-1-(7-cyanopyrazolo[1,5-a]pyridin-4-yl)-5-methyl-3-piperidyl]propanamide To a solution of crude 4-[(3R,5S)-3-amino-5-methyl-1-piperidyl]pyrazolo[1,5-a]pyridine-7-carbonitrile 2,2,2-trifluoroacetate (Example 43, 37 mg, 0.1 mmol), Boc-Ala-OH (28 mg, 0.15 mmol) and DIPEA (52 mg, 68 µl, 0.40 mmol) in DCM (4 mL) was added HATU (76 mg, 200 µmol). The reaction mixture was stirred at rt overnight, then diluted with DCM, washed with sat. $NH_4C_1$ and brine, dried over $Na_2SO_4$ and concentrated to give an oil, which was dissolved in DCM (2 mL) and treated with TFA (1 mL). The mixture was stirred at rt for 1 h, then concentrated to give a crude product which was purified by prep-HPLC to give Example 44 (19 mg) as a white powder. MS: calc'd 327 (MH$^+$), measured 327 (MH$^+$). $^1$H NMR (400 MHz, METHANOL-d$_4$) δ 8.00 (d, J=2.4 Hz, 1H), 7.45 (d, J=7.9 Hz, 1H), 7.02 (d, J=2.4 Hz, 1H), 6.60 (d, J=8.1 Hz, 1H), 4.28 (td, J=2.1, 12.1 Hz, 1H), 4.05 (tt, J=4.1, 11.4 Hz, 1H), 3.86 (q, J=7.0 Hz, 1H), 3.79 (br d, J=8.4 Hz, 1H), 2.60 (t, J=11.9 Hz, 1H), 2.53 (dd, J=11.1, 12.0 Hz, 1H), 2.11 (br d, J=12.3 Hz, 1H), 1.98 (dt, J=7.0, 11.2 Hz, 1H), 1.52 (d, J=7.1 Hz, 3H), 1.24 (q, J=12.1 Hz, 1H), 1.05 (d, J=6.6 Hz, 3H).

Example 45

N-[(3R,5S)-1-(7-cyanopyrazolo[1,5-a]pyridin-4-yl)-5-methyl-3-piperidyl]-2-(dimethylamino)acetamide

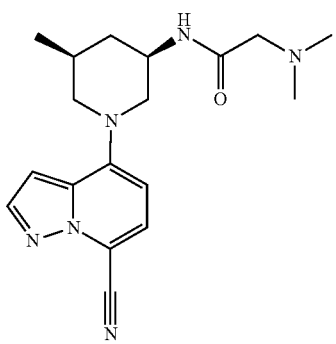 [SMILES: C[C@H]1C[C@@H](NC(=O)CN(C)C)CN(c2ccc(C#N)n3nccc23)C1]

The title compound was prepared according to the following scheme:

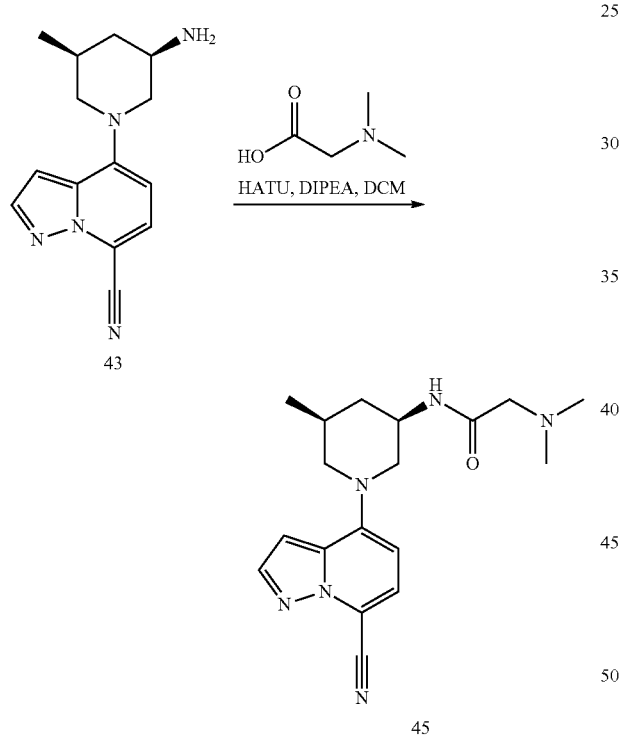

To a solution of crude 4-[(3R,5S)-3-amino-5-methyl-1-piperidyl]pyrazolo[1,5-a]pyridine-7-carbonitrile 2,2,2-trifluoroacetate (Example 43, 37 mg, 0.10 mmol), 2-(dimethylamino)acetic acid (15 mg, 0.15 mmol) and DIPEA (52 mg, 68 μl, 0.40 mmol) in DCM (4 mL) was added HATU (76 mg, 0.20 mmol). The reaction mixture was stirred at rt overnight, then concentrated to give a crude product which was purified by prep-HPLC to give Example 45 (16 mg) as a white powder. MS: calc'd 341 (MH$^+$), measured 341 (MH$^+$). $^1$H NMR (400 MHz, METHANOL-d$_4$) δ 7.98 (d, J=2.4 Hz, 1H), 7.42 (d, J=7.9 Hz, 1H), 6.99 (d, J=2.4 Hz, 1H), 6.57 (d, J=8.1 Hz, 1H), 4.26 (td, J=2.0, 12.2 Hz, 1H), 4.08 (tt, J=4.1, 11.4 Hz, 1H), 3.96 (d, J=4.0 Hz, 2H), 3.85-3.74 (m, 1H), 2.96 (s, 6H), 2.62-2.49 (m, 2H), 2.11 (br d, J=12.3 Hz, 1H), 2.03-1.89 (m, 1H), 1.23 (q, J=12.1 Hz, 1H), 1.04 (d, J=6.6 Hz, 3H).

Example 46

4-[(3R,5S)-3-(cyanomethylamino)-5-methyl-1-piperidyl]pyrazolo[1,5-a]pyridine-7-carbonitrile

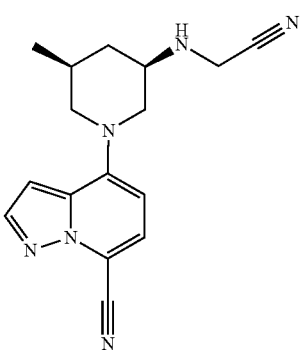 [SMILES: C[C@H]1C[C@@H](NCC#N)CN(c2ccc(C#N)n3nccc23)C1]

The title compound was prepared according to the following scheme:

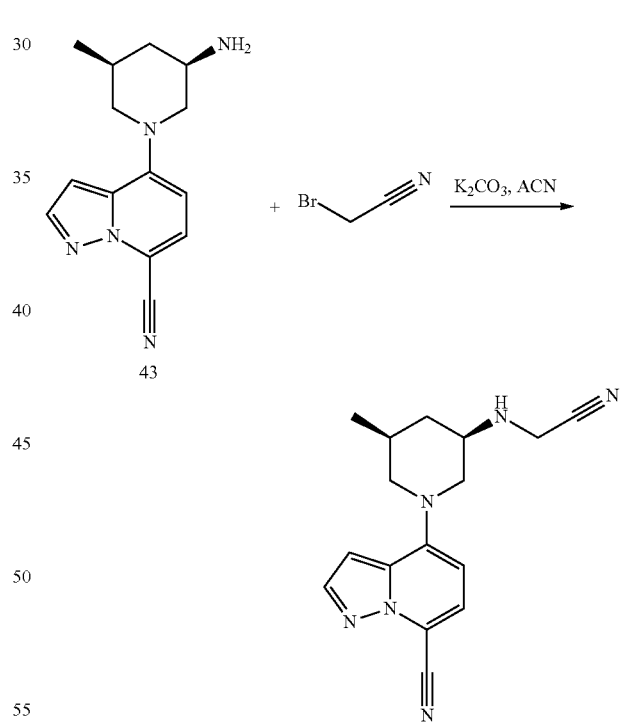

To a solution of crude 4-[(3R,5S)-3-amino-5-methyl-1-piperidyl]pyrazolo[1,5-a]pyridine-7-carbonitrile 2,2,2-trifluoroacetate (Example 43, 37 mg, 0.10 mmol) and K2CO3 in ACN (2 mL) was added 2-bromoacetonitrile (36 mg, 20.9 μl, 0.20 mmol). The resulting suspension was under reflux for 5 h, then diluted with EtOAc, and filtered through celite. The filtrate was concentrated to give an oil which was purified by prep-HPLC to give Example 46 (9 mg) as a light yellow solid. MS: calc'd 295 (MH$^+$), measured 295 (MH$^+$).

$^1$H NMR (400 MHz, METHANOL-d$_4$) δ 8.05 (d, J=2.3 Hz, 1H), 7.49 (d, J=7.9 Hz, 1H), 6.85 (d, J=2.4 Hz, 1H), 6.65 (d, J=7.9 Hz, 1H), 4.21-4.06 (m, 3H), 3.84 (br dd, J=4.2, 12.2 Hz, 1H), 3.34 (br s, 1H), 2.77-2.63 (m, 1H), 2.54 (t, J=11.9 Hz, 1H), 2.35-2.23 (m, 1H), 2.12-1.97 (m, 1H), 1.24-1.12 (m, 1H), 1.08 (d, J=6.5 Hz, 3H).

Example 47

(2R,6R)-4-(7-cyano-3-fluoro-pyrazolo[1,5-a]pyridin-4-yl)-6-methyl-N-(1-methyl-4-piperidyl)morpholine-2-carboxamide The title compound was prepared according to the following scheme:

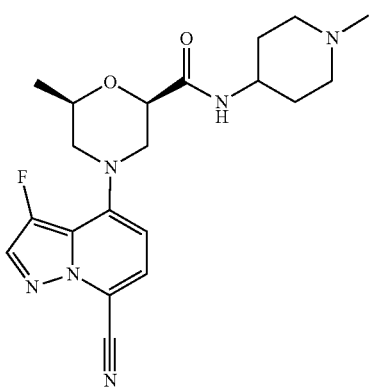 [SMILES: C[C@@H]1CN(c2ccc(C#N)n3ncc(F)c23)C[C@H](C(=O)NC2CCN(C)CC2)O1]

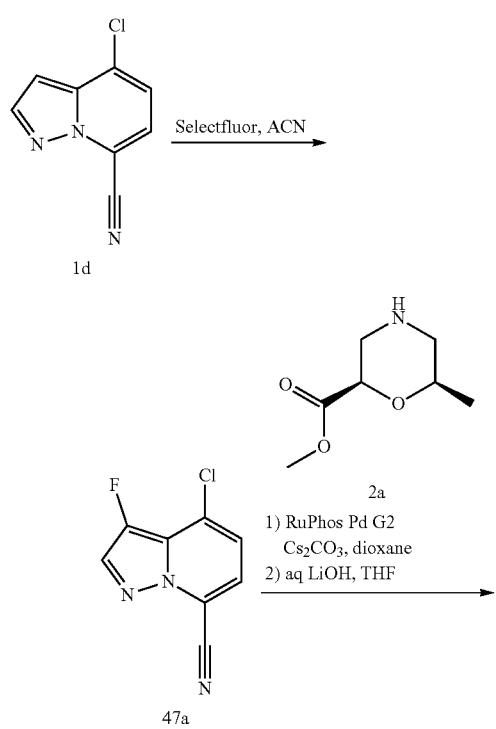

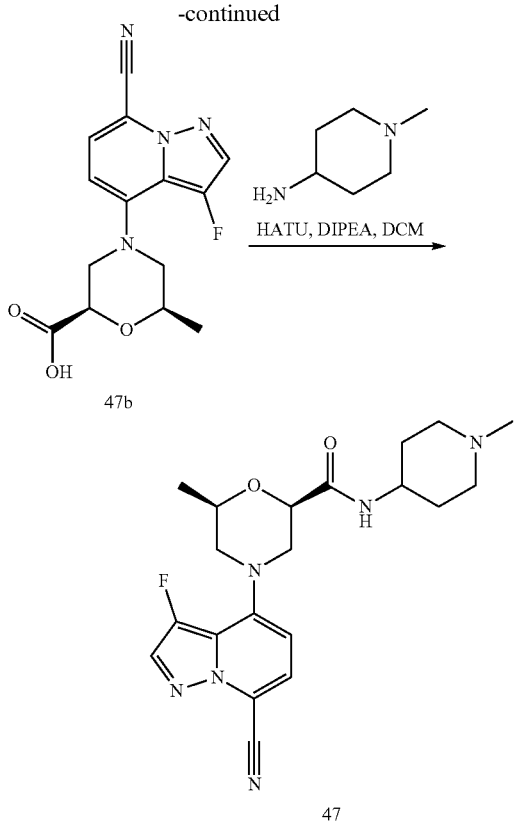

Step 1: preparation of 4-chloro-3-fluoro-pyrazolo[1,5-a]pyridine-7-carbonitrile (Compound 47a)

To a solution of 4-chloropyrazolo[1,5-a]pyridine-7-carbonitrile (compound 1b, 600 mg, 3.38 mmol) in ACN (50 mL) was added Selectfluor (2.39 g, 6.76 mmol). The reaction mixture was stirred at rt for 24 h, LCMS indicated the formation of product. The reaction mixture was then concentrated to remove most ACN, diluted with water (30 mL), extracted with DCM. The organic layer was washed with sat. NH$_4$Cl and brine, dried over Na$_2$SO$_4$, and concentrated to give a crude product which was purified by column chromatography to give compound 67a (419 mg) as light yellow powder. MS: calc'd 196 (MH$^+$), measured 196 (MH$^+$).

Step 2: preparation of (2R,6R)-4-(7-cyano-3-fluoro-pyrazolo[1,5-a]pyridin-4-yl)-6-methyl-morpholine-2-carboxylic acid (Compound 47b)

To a solution of 4-chloro-3-fluoro-pyrazolo[1,5-a]pyridine-7-carbonitrile (compound 47a, 66 mg, 0.34 mmol), methyl (2R,6R)-6-methylmorpholine-2-carboxylate hydrochloride (compound 2a, 73 mg, 0.37 mmol), Cs$_2$CO$_3$ (330 mg, 1.01 mmol) in 1,4-dioxane (5 mL) was added Ruphos Pd G2 (26 mg, 34 µmol). The reaction mixture was heated at 90° C. (oil bath) under N$_2$ for 2 hrs, then cooled to rt and diluted with EtOAc and filtered through celite, the filtrate was concentrated to give a brown oil. The oil was dissolved in THF (2 mL). To the solution was added aq. LiOH (2 M in water, 1 mL, 2.0 mmol). The mixture was stirred at rt for 1 hrs, then pH was adjusted to 1~2 with aq. HCl, then extracted with DCM. The organic layer was washed with brine, dried over Na$_2$SO$_4$, and concentrated to give a crude compound 2b (80 mg) which was directly used in next step. MS: calc'd 305 (MH$^+$), measured 305 (MH$^+$).

Step 3: preparation of (2R,6R)-4-(7-cyano-3-fluoro-pyrazolo[1,5-a]pyridin-4-yl)-6-methyl-N-(1-methyl-4-piperidyl)morpholine-2-carboxamide (Example 47)

To a solution of (2R,6R)-4-(7-cyano-3-fluoro-pyrazolo[1,5-a]pyridin-4-yl)-6-methyl-morpholine-2-carboxylic acid (compound 47b, 61 mg, 0.20 mmol), 1-methylpiperidin-4-amine (34 mg, 38 μL, 0.30 mmol) and DIPEA (103 mg, 140 μL, 0.80 mmol) in DCM (3 mL) was added HATU (152 mg, 0.0.40 mmol). The reaction mixture was stirred at rt overnight, then diluted with DCM, washed with sat. NH$_4$C$_1$ and brine, dried over Na$_2$SO$_4$, and concentrated to give a crude product which was purified by prep-HPLC to give Example 47 (15 mg) as a white powder. MS: calc'd 401 (MH$^+$), measured 401 (MH$^+$). $^1$H NMR (400 MHz, METHANOL) δ 8.01 (d, J=3.7 Hz, 1H), 7.43 (d, J=7.9 Hz, 1H), 6.55 (d, J=7.9 Hz, 1H), 4.30 (dd, J=2.6, 10.8 Hz, 1H), 4.07-3.93 (m, 2H), 3.87 (br d, J=12.3 Hz, 1H), 3.57 (br d, J=12.0 Hz, 3H), 3.18-3.06 (m, 2H), 2.96-2.85 (m, 3H), 2.80 (t, J=11.5 Hz, 1H), 2.72-2.63 (m, 1H), 2.19-2.06 (m, 2H), 2.05-1.80 (m, 2H), 1.33 (d, J=6.2 Hz, 3H).

Example 48

The following tests were carried out in order to determine the activity of the compounds of formula (I) in HEK293-Blue-hTLR-7/8/9 cells assay.
HEK293-Blue-hTLR-7 Cells Assay:

A stable HEK293-Blue-hTLR-7 cell line was purchased from InvivoGen (Cat. #: hkb-htlr7, San Diego, California, USA). These cells were originally designed for studying the stimulation of human TLR7 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR7 cells with TLR7 ligands. Therefore the reporter expression was declined by TLR7 antagonist under the stimulation of a ligand, such as R848 (Resiquimod), for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

HEK293-Blue-hTLR7 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM R848 in above DMEM, perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR7 activation leads to downstream NF-κB activation has been widely accepted, and therefore similar reporter assay was modified for evaluating TLR7 antagonist.
HEK293-Blue-hTLR-8 Cells Assay:

A stable HEK293-Blue-hTLR-8 cell line was purchased from InvivoGen (Cat. #: hkb-htlr8, San Diego, California, USA). These cells were originally designed for studying the stimulation of human TLR8 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR8 cells with TLR8 ligands. Therefore the reporter expression was declined by TLR8 antagonist under the stimulation of a ligand, such as R848, for incubation of 20 hrs. The cell culture supernatant SEAP reporter activity was determined using QUANTI-Blue™ kit (Cat. #: rep-qb1, Invivogen, San Diego, Ca, USA) at a wavelength of 640 nm, a detection medium that turns purple or blue in the presence of alkaline phosphatase.

HEK293-Blue-hTLR8 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 60 uM R848 in above DMEM, perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR8 activation leads to downstream NF-κB activation has been widely accepted, and therefore similar reporter assay was modified for evaluating TLR8 antagonist.
HEK293-Blue-hTLR-9 Cells Assay:

A stable HEK293-Blue-hTLR-9 cell line was purchased from InvivoGen (Cat. #: hkb-htlr9, San Diego, California, USA). These cells were originally designed for studying the stimulation of human TLR9 by monitoring the activation of NF-κB. A SEAP (secreted embryonic alkaline phosphatase) reporter gene was placed under the control of the IFN-β minimal promoter fused to five NF-κB and AP-1-binding sites. The SEAP was induced by activating NF-κB and AP-1 via stimulating HEK-Blue hTLR9 cells with TLR9 ligands. Therefore the reporter expression was declined by TLR9 antagonist under the stimulation of a ligand, such as ODN2006 (Cat. #: tlrl-2006-1, Invivogen, San Diego, California, USA), for incubation of 20 hrs. The cell culture supernatant SEAP reporter activity was determined using QUANTI-Blue™ kit (Cat. #: rep-qb1, Invivogen, San Diego, California, USA) at a wavelength of 640 nm, a detection medium that turns purple or blue in the presence of alkaline phosphatase.

HEK293-Blue-hTLR9 cells were incubated at a density of 250,000~450,000 cells/mL in a volume of 170 μL in a 96-well plate in Dulbecco's Modified Eagle's medium (DMEM) containing 4.5 g/L glucose, 50 U/mL penicillin, 50 mg/mL streptomycin, 100 mg/mL Normocin, 2 mM L-glutamine, 10% (v/v) heat-inactivated fetal bovine serum with addition of 20 μL test compound in a serial dilution in the presence of final DMSO at 1% and 10 μL of 20 uM ODN2006 in above DMEM, perform incubation under 37° C. in a CO$_2$ incubator for 20 hrs. Then 20 μL of the supernatant from each well was incubated with 180 μL Quanti-blue substrate solution at 37° C. for 2 hrs and the absorbance was read at 620~655 nm using a spectrophotometer. The signalling pathway that TLR9 activation leads to downstream NF-κB activation has been widely accepted, and therefore similar reporter assay was modified for evaluating TLR9 antagonist.

The compounds of formula (I) have human TLR7 and/or TLR8 inhibitory activities (IC$_{50}$ value)<1 μM, particularly <0.020 μM. Activity data of the compounds of the present invention were shown in Table 1.

TABLE 1

The activity of the compounds of present invention in HEK293-Blue-hTLR-7/8/9 cells assays

| Example | TLR7 IC$_{50}$ (μM) | TLR8 IC$_{50}$ (μM) | TLR9 IC$_{50}$ (μM) |
| --- | --- | --- | --- |
| 1 | 0.017 | 0.007 | 15 |
| 2 | 0.091 | 0.16 | >100 |
| 3 | 0.16 | 0.095 | 36 |
| 4 | 0.41 | 0.91 | >100 |
| 5 | 0.073 | 0.047 | 77 |
| 6 | 0.016 | 0.011 | 4.8 |
| 7 | 0.067 | 0.050 | 58 |
| 8 | 0.19 | 0.52 | 70 |
| 9 | 0.65 | 0.86 | >100 |
| 12 | 0.21 | 0.32 | 42 |
| 13 | 0.49 | 0.57 | >100 |
| 14 | 0.007 | 0.030 | 1.6 |
| 15 | 0.22 | 0.71 | >100 |
| 16 | 0.46 | 0.21 | >100 |
| 17 | 0.36 | 0.10 | 33 |
| 18 | 0.055 | 0.10 | >100 |
| 19 | 0.099 | 0.027 | 16 |
| 20 | 0.35 | 0.19 | 71 |
| 21 | 0.42 | 0.57 | >100 |
| 22 | 0.010 | 0.025 | 18 |
| 23 | 0.027 | 0.074 | >100 |
| 24 | 0.043 | 0.037 | 13 |
| 25 | 0.15 | 0.61 | 25 |
| 26 | 0.020 | 0.093 | 13 |
| 27 | 0.063 | 0.37 | 6.8 |
| 28 | 0.32 | 0.097 | 1.7 |
| 31 | 0.050 | 0.072 | 1.1 |
| 32 | 0.031 | 0.031 | 9.7 |
| 33 | 0.004 | 0.058 | 7.7 |
| 34 | 0.010 | 0.098 | 11 |
| 35 | 0.004 | 0.038 | 11 |
| 36 | 0.13 | 0.83 | 12 |
| 37 | 0.009 | 0.018 | 6.8 |
| 38 | 0.028 | 0.007 | 36 |
| 39 | 0.030 | 0.033 | 19 |
| 40 | 0.21 | 0.38 | 48 |
| 41 | 0.046 | 0.14 | 11 |
| 42 | 0.012 | 0.062 | 1.8 |
| 43 | 0.034 | 0.012 | 10 |
| 44 | 0.064 | 0.14 | 10 |
| 46 | 0.17 | 0.24 | 31 |
| 47 | 0.008 | 0.005 | 14 |

The invention claimed is:
1. A compound of formula (I),

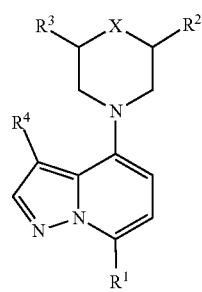

wherein:
R$^1$ is cyano, C$_{1-6}$alkyl, halogen, haloC$_{1-6}$alkyl or nitro;
R$^2$ is C$_{1-6}$alkyl or haloC$_{1-6}$alkyl;
R$^3$ is —NHR$^{3a}$ or —COR$^{3b}$, wherein:
R$^{3a}$ is H, aminoC$_{1-6}$alkylcarbonyl, (C$_{1-6}$alkyl)$_2$aminoC$_{1-6}$alkylcarbonyl or cyanoC$_{1-6}$alkyl;
R$^{3b}$ is (heterocyclylcarbonyl)phenylamino, (hydroxyC$_{1-6}$alkoxy)C$_{1-6}$alkylamino, adamantylamino, aminoC$_{1-6}$alkylamino, C$_{1-6}$alkoxyC$_{1-6}$alkylamino, C$_{1-6}$alkylamino, C$_{1-6}$alkylpyrazolylamino, cyanoC$_{3-7}$cycloalkylamino, heterocyclyl, heterocyclylamino, heterocyclylC$_{1-6}$alkylamino, hydroxyC$_{1-6}$alkylamino, hydroxyC$_{1-6}$alkylC$_{3-7}$cycloalkylamino, hydroxyC$_{3-7}$cycloalkylamino or pyridylamino;
R$^4$ is H or halogen; and
X is O or CH$_2$;
or a pharmaceutically acceptable salt, enantiomer or diastereomer thereof.

2. A compound according to claim 1, wherein R$^1$ is cyano or halogen.

3. A compound according to claim 2, wherein:
R$^1$ is cyano or halogen;
R$^2$ is C$_{1-6}$alkyl;
R$^3$ is —NHR$^{3a}$ or —COR$^{3b}$, wherein:
R$^{3a}$ is H, aminoC$_{1-6}$alkylcarbonyl, (C$_{1-6}$alkyl)$_2$aminoC$_{1-6}$alkylcarbonyl or cyanoC$_{1-6}$alkyl;
R$^{3b}$ is (C$_{1-6}$alkylmorpholinyl)C$_{1-6}$alkylamino, (hydroxyC$_{1-6}$alkoxy)C$_{1-6}$alkylamino, (piperazinylcarbonyl)phenylamino, adamantylamino, aminoazetidinyl, aminoC$_{1-6}$alkylamino, azabicyclo[2.2.1]heptanylamino, azabicyclo[3.1.0]hexanylamino, azabicyclo[3.2.1]octanylamino, azabicyclo[3.3.1]nonanylamino, azaspiro[3.3]heptanylamino, azepanylamino, C$_{1-6}$alkoxyC$_{1-6}$alkylamino, C$_{1-6}$alkylamino, C$_{1-6}$alkylazabicyclo[2.2.2]octanylamino, C$_{1-6}$alkylazabicyclo[3.2.1]octanylamino, C$_{1-6}$alkylazabicyclo[3.3.1]nonanylamino, C$_{1-6}$alkylazaspiro[2.4]heptanylamino, C$_{1-6}$alkylpiperidylamino, C$_{1-6}$alkylpyrazolylamino, cyanoC$_{3-7}$cycloalkylamino, diazaspiro[5.5]undecanyl, halopyrrolidinylamino, halopyrrolidinylC$_{1-6}$alkylamino, hydroxyC$_{1-6}$alkylamino, hydroxyC$_{1-6}$alkylC$_{3-7}$cycloalkylamino, hydroxyC$_{3-7}$cycloalkylamino, oxaazabicyclo[3.3.1]nonanylamino, piperidylamino, pyridylamino, pyrrolidinylamino, pyrrolidinylC$_{1-6}$alkylamino or tetrahydropyranylamino;
R$^4$ is H or halogen; and
X is O or CH$_2$;
or a pharmaceutically acceptable salt, enantiomer or diastereomer thereof.

4. A compound according to claim 3, wherein R$^1$ is cyano or chloro.

5. A compound according to claim 4, wherein R$^1$ is cyano.

6. A compound according to claim 4, wherein R$^2$ is methyl.

7. A compound according to claim 3, wherein:
R$^3$ is —NHR$^{3a}$ or —COR$^{3b}$, wherein R$^{3a}$ is H, aminoethylcarbonyl, (dimethylamino)methylcarbonyl or cyanomethyl; R$^{3b}$ is (hydroxyethoxy)ethylamino, (hydroxymethyl)bicyclo[1.1.1]pentanylamino, (methylmorpholinyl)methylamino, (piperazinylcarbonyl)phenylamino, 2-azabicyclo[2.2.1]heptan-5-ylamino, 2-azaspiro[3.3]heptan-6-ylamino, 2-methyl-2-azabicyclo[2.2.2]octan-5-ylamino, 3,9-diazaspiro[5.5]undecanyl, 3-azabicyclo[3.1.0]hexan-6-ylamino, 3-azabicyclo[3.2.1]octan-8-ylamino, 3-azabicyclo[3.3.1]nonan-9-ylamino, 3-oxa-7-azabicyclo[3.3.1]nonan-9-ylamino, 3-oxa-9-azabicyclo[3.3.1]nonan-7- ylamino, 5-methyl-5-azaspiro[2.4]heptan-7-ylamino, 8-azabicyclo[3.2.1]octan-3-ylamino, 8-methyl-8-azabicyclo[3.2.1]octan-3-ylamino, 9-azabicyclo[3.3.1]nonan-3-ylamino, 9-methyl-9-azabicyclo[3.3.1]nonan-3-ylamino, adamantylamino, aminoazetidinyl, aminodimethylethylamino, aminodimethylpropylamino, azepan-4-ylamino, cyanocyclopropylamino, difluoropyrrolidinylmethylamino, dimethylpropylamino, fluoropyrrolidinylamino, hydroxybutylamino, hydroxycyclohexylamino, hydroxydimethylethylamino, methoxyethylamino, methylpiperidylamino, methylpyrazolylamino, piperidylamino, pyridylamino, pyrrolidinylamino, pyrrolidinylmethylamino or tetrahydropyranylamino.

8. A compound according to claim 7, wherein $R^3$ is —$COR^{3b}$, wherein $R^{3b}$ is methylpiperidylamino, azepanylamino or 3-azabicyclo[3.3.1]nonan-9-ylamino.

9. A compound according to claim 8, wherein $R^4$ is H or fluoro.

10. A compound according to claim 9, wherein X is O.

11. A compound according to claim 2, selected from:
(2R,6R)-4-(7-cyanopyrazolo[1,5-a]pyridin-4-yl)-6-methyl-N-(1-methyl-4-piperidyl)morpholine-2-carboxamide;
(2R,6R)-4-(7-cyanopyrazolo[1,5-a]pyridin-4-yl)-N-[(3S,4R)-4-fluoropyrrolidin-3-yl]-6-methyl-morpholine-2-carboxamide;
(2R,6R)-N-(2-azaspiro[3.3]heptan-6-yl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-6-methyl-N-tetrahydropyran-4-yl-morpholine-2-carboxamide;
Cis-(2R,6R)-4-(7-cyanopyrazolo[1,5-a]pyridin-4-yl)-6-methyl-N-(4-fluoropyrrolidin-3-yl) morpholine-2-carboxamide;
(2R,6R)-N-(azepan-4-yl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-6-methyl-N-[(4-methylmorpholin-2-yl)methyl]morpholine-2-carboxamide;
4-[(2R,6R)-2-(3-aminoazetidine-1-carbonyl)-6-methyl-morpholin-4-yl]pyrazolo[1,5-a]pyridine-7-carbonitrile;
(2R,6R)-4-(7-cyanopyrazolo[1,5-a]pyridin-4-yl)-N-(2-methoxyethyl)-6-methyl-morpholine-2-carboxamide;
(2R,6R)-4-(7-cyanopyrazolo[1,5-a]pyridin-4-yl)-N-[2-(2-hydroxyethoxy)ethyl]-6-methyl-morpholine-2-carboxamide;
(2R,6R)-N-(1-cyanocyclopropyl)-4-(7-cyanopyrazolo[1,5-a]pyridin-4-yl)-6-methyl-morpholine-2-carboxamide;
(2R,6R)-N-(1-adamantyl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-N-(2-hydroxybutyl)-6-methyl-morpholine-2-carboxamide;
(2R,6R)-N-(9-azabicyclo[3.3.1]nonan-3-yl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-N-[3-(hydroxymethyl)-1-bicyclo[1.1.1]pentanyl]-6-methyl-morpholine-2-carboxamide;
(2R,6R)-4-(7-cyanopyrazolo[1,5-a]pyridin-4-yl)-N-(2-hydroxy-1,1-dimethyl-ethyl)-6-methyl-morpholine-2-carboxamide;
(2R,6R)-4-(7-cyanopyrazolo[1,5-a]pyridin-4-yl)-N-(1,1-dimethylpropyl)-6-methyl-morpholine-2-carboxamide;
(2R,6R)-4-(7-cyanopyrazolo[1,5-a]pyridin-4-yl)-N-[(4,4-difluoropyrrolidin-3-yl)methyl]-6-methyl-morpholine-2-carboxamide;
(2R,6R)-4-(7-cyanopyrazolo[1,5-a]pyridin-4-yl)-6-methyl-N-(4-methyl-4-piperidyl)morpholine-2-carboxamide;
Cis-(2R,6R)-4-(7-cyanopyrazolo[1,5-a]pyridin-4-yl)-N-(4-hydroxycyclohexyl)-6-methyl-morpholine-2-carboxamide;
Trans-(2R,6R)-4-(7-cyanopyrazolo[1,5-a]pyridin-4-yl)-N-(4-hydroxycyclohexyl)-6-methyl-morpholine-2-carboxamide;
Endo-(2R,6R)-4-(7-cyanopyrazolo[1,5-a]pyridin-4-yl)-6-methyl-N-[3-oxa-9-azabicyclo[3.3.1]nonan-7-yl]morpholine-2-carboxamide;
Exo-(2R,6R)-N-[8-azabicyclo[3.2.1]octan-3-yl]-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-6-methyl-N-(4-piperidyl)morpholine-2-carboxamide;
(2R,6R)-4-(7-cyanopyrazolo[1,5-a]pyridin-4-yl)-6-methyl-N-pyrrolidin-3-yl-morpholine-2-carboxamide;
(2R,6R)-N-(3-azabicyclo[3.2.1]octan-8-yl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-6-methyl-N-(3-oxa-7-azabicyclo[3.3.1]nonan-9-yl)morpholine-2-carboxamide;
4-[(2R,6R)-2-(3,9-diazaspiro[5.5]undecane-3-carbonyl)-6-methyl-morpholin-4-yl]pyrazolo[1,5-a]pyridine-7-carbonitrile;
(2R,6R)-4-(7-cyanopyrazolo[1,5-a]pyridin-4-yl)-6-methyl-N-(4-pyridyl)morpholine-2-carboxamide;
(2R,6R)-4-(7-cyanopyrazolo[1,5-a]pyridin-4-yl)-6-methyl-N-(1-methylpyrazol-3-yl)morpholine-2-carboxamide;
Trans-(2R,6R)-N-(3-azabicyclo[3.1.0]hexan-6-yl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-6-methyl-N-(5-methyl-5-azaspiro[2.4]heptan-7-yl)morpholine-2-carboxamide;
(2R,6R)-4-(7-cyanopyrazolo[1,5-a]pyridin-4-yl)-6-methyl-N-(8-methyl-8-azabicyclo[3.2.1]octan-3-yl) morpholine-2-carboxamide;
(2R,6R)-4-(7-cyanopyrazolo[1,5-a]pyridin-4-yl)-6-methyl-N-(2-methyl-2-azabicyclo[2.2.2]octan-5-yl) morpholine-2-carboxamide;
(2R,6R)-4-(7-cyanopyrazolo[1,5-a]pyridin-4-yl)-6-methyl-N-(9-methyl-9-azabicyclo[3.3.1]nonan-3-yl) morpholine-2-carboxamide;
(2R,6R)-N-(2-azabicyclo[2.2.1]heptan-5-yl)-4-(7-cyanopyrazolo[1,5-a]pyridin-4-yl)-6-methyl-morpholine-2-carboxamide;
(2R,6R)-N-(3-azabicyclo[3.3.1]nonan-9-yl)-4-(7-cyanopyrazolo[1,5-a]pyridin-4-yl)-6-methyl-morpholine-2-carboxamide;
(2R,6R)-4-(7-chloropyrazolo[1,5-a]pyridin-4-yl)-6-methyl-N-(1-methyl-4-piperidyl)morpholine-2-carboxamide;
(2R,6R)-N-(3-amino-2,2-dimethyl-propyl)-4-(7-cyanopyrazolo[1,5-a]pyridin-4-yl)-6-methyl-morpholine-2-carboxamide;
(2R,6R)-4-(7-cyanopyrazolo[1,5-a]pyridin-4-yl)-6-methyl-N-(pyrrolidin-3-ylmethyl)morpholine-2-carboxamide;

(2R,6R)-N-(2-amino-1,1-dimethyl-ethyl)-4-(7-cyanopyrazolo[1,5-a]pyridin-4-yl)-6-methyl-morpholine-2-carboxamide;

(2R,6R)-4-(7-cyanopyrazolo[1,5-a]pyridin-4-yl)-6-methyl-N-[4-(piperazine-1-carbonyl)phenyl]morpholine-2-carboxamide;

4-[(3R,5S)-3-amino-5-methyl-1-piperidyl]pyrazolo[1,5-a]pyridine-7-carbonitrile;

(2S)-2-amino-N-[(3R,5S)-1-(7-cyanopyrazolo[1,5-a]pyridin-4-yl)-5-methyl-3-piperidyl]propanamide;

N-[(3R,5S)-1-(7-cyanopyrazolo[1,5-a]pyridin-4-yl)-5-methyl-3-piperidyl]-2-(dimethylamino)acetamide;

4-[(3R,5S)-3-(cyanomethylamino)-5-methyl-1-piperidyl]pyrazolo[1,5-a]pyridine-7-carbonitrile; and (2R,6R)-4-(7-cyano-3-fluoro-pyrazolo[1,5-a]pyridin-4-yl)-6-methyl-N-(1-methyl-4-piperidyl)morpholine-2-carboxamide;

or a pharmaceutically acceptable salt, enantiomer or diastereomer thereof.

12. A compound according to claim 11, selected from:
(2R,6R)-4-(7-cyanopyrazolo[1,5-a]pyridin-4-yl)-6-methyl-N-(1-methyl-4-piperidyl)morpholine-2-carboxamide;

(2R,6R)-N-(azepan-4-yl)-4-(7-cyanopyrazolo[1,5-a]pyridin-4-yl)-6-methyl-morpholine-2-carboxamide;

(2R,6R)-N-(3-azabicyclo[3.3.1]nonan-9-yl)-4-(7-cyanopyrazolo[1,5-a]pyridin-4-yl)-6-methyl-morpholine-2-carboxamide; and (2R,6R)-4-(7-cyano-3-fluoro-pyrazolo[1,5-a]pyridin-4-yl)-6-methyl-N-(1-methyl-4-piperidyl)morpholine-2-carboxamide;

or a pharmaceutically acceptable salt, enantiomer or diastereomer thereof.

13. A process for preparing a compound according to claim 1 comprising any of the following steps:

a) reacting a compound of formula (IX),

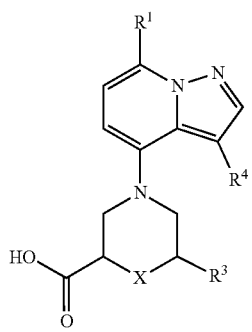

(IX)

with $R_5R_6NH$ in the presence of a coupling reagent;

b) reacting a compound of formula (XII),

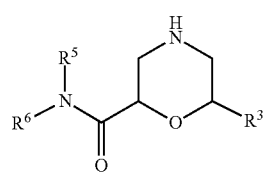

(XII)

with compound of formula (VII),

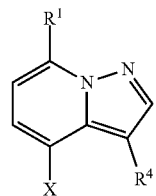

(VII)

in the presence of a catalyst and a base;

c) reacting a compound of formula (XV),

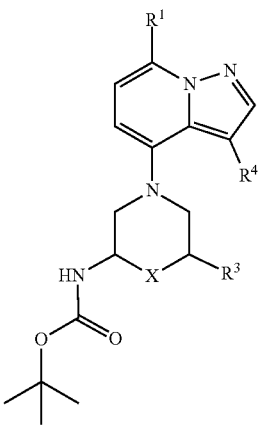

(XV)

in the presence of an acid;

d) reacting a compound of formula (III),

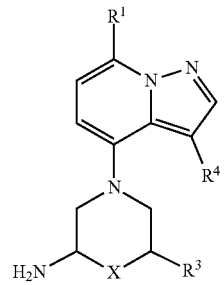

(III)

with an acid (XVI),

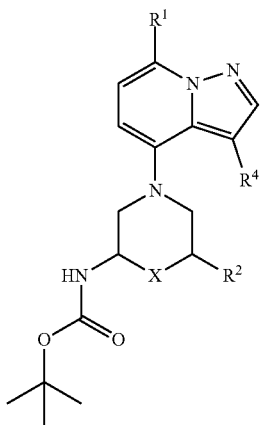

(XVI)

in the presence of a coupling reagent;
wherein:
the coupling reagent is HATU; the catalyst is Ruphos Pd-G2 and the base is $Cs_2CO_3$;
the acid is $TFA/CH_2Cl_2$ or HCl in dioxane;

$R^5$ and $R^6$ are independently selected from H, (hydroxy$C_{1-6}$alkoxy)$C_{1-6}$alkyl, adamantyl, amino$C_{1-6}$alkyl, $C_{1-6}$alkoxy$C_{1-6}$alkyl, $C_{1-6}$alkyl, $C_{1-6}$alkylpyrazolyl, cyano$C_{3-7}$cycloalkyl, hydroxy$C_{1-6}$alkyl, hydroxy$C_{1-6}$alkyl$C_{3-7}$cycloalkyl, pyridyl, hydroxy$C_{3-7}$cycloalkyl, heterocyclyl$C_{1-6}$alkyl, (heterocyclylcarbonyl)phenyl or heterocyclyl; or
$R^5$ and $R^6$ together with the nitrogen they are attached to form a heterocyclyl; and
$R^7$ is H, $C_{1-6}$alkyl, amino$C_{1-6}$alkyl, amino$C_{1-6}$alkyl, $C_{1-6}$alkyl)$_2$amino$C_{1-6}$alkyl or heterocyclyl.

14. A pharmaceutical composition comprising a compound in accordance with claim 1 and a therapeutically inert carrier.

15. A method for treating systemic lupus erythematosus or lupus nephritis, which method comprises administering to a subject in need thereof a therapeutically effective amount of a compound as defined in claim 1.

16. A method for treating systemic lupus erythematosus or lupus nephritis, which method comprises administering to a subject in need thereof a therapeutically effective amount of a compound as defined in claim 12.

17. A pharmaceutical composition comprising a compound in accordance with claim 12 and a therapeutically inert carrier.

* * * * *